United States Patent [19]
Harada et al.

[11] Patent Number: 6,090,544
[45] Date of Patent: *Jul. 18, 2000

[54] METHODS AND COMPOSITIONS FOR IDENTIFYING MORPHOGEN ANALOGS

[75] Inventors: Shun-ichi Harada, North Wales; Gideon A. Rodan, Bryn Mawr, both of Pa.; Kuber T. Sampath, Holliston, Mass.

[73] Assignee: Creative BioMolecules, Inc., Hopkington, Mass.

[ * ] Notice: This patent is subject to a terminal disclaimer.

[21] Appl. No.: 08/764,522

[22] Filed: Dec. 12, 1996

Related U.S. Application Data

[63] Continuation-in-part of application No. 08/507,598, Jul. 26, 1995.

[51] Int. Cl.$^7$ .............................. C12N 5/10; C12N 15/11; C12Q 1/68
[52] U.S. Cl. .................................. 435/6; 435/4; 435/325; 536/24.1
[58] Field of Search .................................. 435/6, 4, 325; 536/24.1

[56] References Cited

U.S. PATENT DOCUMENTS

| | | | |
|---|---|---|---|
| 5,578,708 | 11/1996 | Okazaki et al. | 530/399 |
| 5,665,543 | 9/1997 | Foulkes et al. | 435/6 |

FOREIGN PATENT DOCUMENTS

| | | |
|---|---|---|
| WO93/05172 | 3/1993 | WIPO . |
| WO95/11983 | 5/1995 | WIPO . |
| WO95/14104 | 5/1995 | WIPO . |
| WO95/33831 | 12/1995 | WIPO . |
| WO96/08197 | 3/1996 | WIPO . |
| WO96/34101 | 10/1996 | WIPO . |
| WO96/34951 | 11/1996 | WIPO . |
| WO96/38590 | 12/1996 | WIPO . |
| WO97/05241 | 2/1997 | WIPO . |
| WO97/05285 | 2/1997 | WIPO . |

OTHER PUBLICATIONS

Harada et al., (Nov. 1997), "Osteogenic Protein–1 Up–Regulation of the Collagen X Promoter Activity is Mediated by a MEF–2–Like Sequence and Requires an Adjacent AP–1 Sequence", *Molecular Endocrinology*, vol. 11, No. 12, pp. 1832–1845.

Satoh et al., (1993), "Effect of Drugs on Gene Expression in Mammalian Cells: A Highly Efficient Procedure to Test Large Numbers of Samples", *Nucleic Acids Research*, vol. 21, No. 18, pp. 4429–4430.

Thomas et al., (Jul. 28, 1995), "Sequence Comparison of Three Mammalian Type–X Collagen Promoters and Preliminary Functional Analysis of the Human Promoter", *Gene*, vol. 2, No. 160, pp. 291–296.

Harada et al., "Osteogenic Protein–1 Upregulation of the Mouse Collagen X Promoter Activity is Mediated by a MEF–2 Like Sequence and Requires an Adjacent AP–1 Sequence", 2nd International Conference of Bone Morphogenetic Proteins, Sacramento, CA, Jun. 4–8, 1997.

Ghosh–Choudhury et al., "Immortalized Murine Osteoblasts Derived from BMP 2–T–Antigen Expressing Transgenic Mice", *Endocrinology*, 137:331–339 (1997).

Harris et al., "Recombinant Bone Morphogenetic Protein 2 Accelerates Bone Cell Differentiation and Stimulates BMP–2 mRNA Expression and BMP–2 Promoter Activity in Primary Fetal Rat Calvarial Osteoblast Cultures" *Molecular and Cellular Differentiation* 3:137–155 (1995).

Lee et al. (1987), "Purified Transcription Factor AP–1 Interacts with TPA–Inducible Enhancer Elements," *Cell* 49:741–752.

Yoon et al. (1988), "Characterization of the Rat Osteocalcin Gene: Stimulation of Promoter Activity by 1,25–Dihydroxyvitamin $D_3$", *Biochemistry*, 27:8521–8526.

Ohta et al. (1992), "Bone Morphogenetic Proteins (BMP–2 and BMP–3) Induce the Late Phase Expression of the Proto–Oncogene c–fos in Murine Osteoblastic MC3T3–E1 Cells," *FEBS* 314:356–360.

Wang et al. (1992), "Bone and Haematopoietic Defects in Mice Lacking c–fos," *Nature* 360:741–745.

Yu et al. (1992), "Human Myocyte–Specific Enhancer Factor 2 Comprises a Group of Tissue–Restricted MADS Box Transcription Factors," *Genes & Devel.* 6:1783–1798.

Asahina et al. (1993), "Human Osteogenic Protein–1 Induces Both Chondroblastic and Osteoblastic Differentiation of Osteoprogenitor Cells Derived From Newborn Rat Calvaria," *J. Cell Biol.* 123:921–933.

Chen et al. (1993), "Bovine Articular Chondrocytes Do Not Undergo Hypertrophy When Cultured In the Presence of Serum and Osteogenic Protein–1," *Biochem. & Biophys. Res. Commun.* 197:1253–1259.

Elima et al. (1993), "The Mouse Collagen X Gene: Complete Nucleotide Sequence, Exon Structure and Expression Pattern," *Biochem. J.* 289:247–253.

(List continued on next page.)

*Primary Examiner*—Johnny F. Railey, II
*Attorney, Agent, or Firm*—Michel Morency; Ivor R. Elrifi; Mintz, Levin, et al.

[57] ABSTRACT

Disclosed herein are methods and compositions for identifying morphogen analogs. The preferred methods and compositions relate to the discovery that morphogen upregulation of the mouse type X collagen promoter activity is mediated by a MEF-2 like sequence and requires an adjacent AP-1 sequence. Certain methods rest on the use of test cells comprising DNA defining a morphogen-responsive transcription activating element operatively associated with a reporter gene. Other methods rest on the use of DNAs for measuring morphogen-inducible DNA-binding. In certain preferred embodiments, the methods and DNAs involve an osteogenic protein 1 (OP-1) responsive transcription activating element. Substances that mediate interaction with and/or activate the OP-1 responsive transcription activating element are considered herein likely to be useful for reproducing in vivo effects of morphogens such as OP-1.

9 Claims, 12 Drawing Sheets

OTHER PUBLICATIONS

Knutsen et al. (1993), "Osteogenic Protein–1 Stimulates Proliferation and Differentiation of Human Bone Cells In Vitro," *Biochem. and Biophys. Res. Commun.* 194:1352–1358.

LuValle et al. (1993), "Multiple Negative Elements in a Gene that Codes for an Extracellular Matrix Protein, Collagen X, Restrict Expression to Hypertrophic Chondrocytes," *J. Cell Biol.* 5:1173–1179.

Michiels et al. (1993), "Retroviruses and Oncogenes Associated With Osteosarcomas," *Osteosarcoma In Adolescents and Young Adults* G. Bennett Humphrey (ed.), Kluwer Academic Publishers, Boston, MA.

Topping et al. (1993), "Bone Morphogenetic Proteins Increase Type X Collagen Synthesis in vivo," *J. Cell. Biochem.* Abstract No. 17E:166.

Vainio et al. (1993), "Identification of BMP–4 as a Signal Mediating Secondary Induction Between Epithelial and Mesenchymal Tissues During Early Tooth Development," *Cell* 75:45–58.

Bogdanovic et al (1994), "Upstream Regulatory Elements Necessary for Expression of the Rat COL1A1 Promoter in Transgenic Mice," *J. Bone & Mineral Res.* 9:285–292.

Galera et al. (1994), "C–Krox a Transcriptional Regulator of Type I Collagen Gene Expression is Preferentially Expressed in Skin," *Proc. Natl. Acad. Sci. (USA)* 91:9372–9376.

Katagiri et al. (1994), "Bone Morphogenetic Protein–2 Converts the Differentiation Pathway of C2C12 Myoblasts into the Osteoblast Lineage," *J. Cell Biol.* 127:1755–1766.

Liu et al. (1994), "Simultaneous Detection of Multiple Bone–Related mRNAs and Protein Expression During Osteoblast Differentiation: Polymerase Chain Reaction and Immunocytochemical Studies At The Single Cell Level," *Dev. Biol.* 166:220–234.

Maliakal et al. (1994), "Osteogenic Protein–1 (BMP–7) Inhibits Cell Proliferation and Stimulates the Expression of Markers Characteristic of Osteoblast Phenotype In Rat Osteosarcoma (17/2.8) Cells," *Growth Factors* 11:227–234.

Rosen et al. (1994), "Responsiveness of Clonal Limb Bud Cell Lines to Bone Morphogenetic Protein 2 Reveals a Sequential Relationship Between Cartilage and Bone Cell Phenotypes," *J. Bone & Min. Res.* 9:1759–1768.

Strong et al. (1994), "The Effects of the Insulin–Like Growth Factors and Transforming Growth Factor β on the Jun Proto–Oncogene Family in MC3T3–E1 Cells," *Calcif. Tissue Int.* 55:311–315.

Carey et al. (1995), "Expression of Bone Morphogenetic Protein–6 Messenger RNA in Bovine Growth Plate Chondrocytes of Different Size," *J. Bone & Min. Res.* 10:401–405.

Chen et al. (1995), "Osteogenic Protein–1 Promotes Growth and Maturation of Chick Sternal Chondrocytes in Serum–Free Cultures," *J. Cell Sci.* 108:105–114.

Ducy et al. (1995), "Two distinct osteoblast specific cis–acting elements control expression of a mouse osteocalcin gene," *Mol. Cell. Biol.* 15:1858–1869.

Geoffroy et al. (1995), "A PEBP2 alpha/AML–1–Related Factor Increases Osteocalcin Promoter Activity Through its Binding to an Osteoblast–Specific cis–Acting Element," *J. Biol. Chem. (US)* 270:30973–30979.

Harada et al. (1995), "Induction of Vascular Endothelial Growth Factor by Osteogenic Protein 1 in vitro and in vivo," *Am. Soc. Bone & Min. Res.* 10:Suppl. 1, Abstract No. T268.

Harada et al. (1995), "Osteogenic Protein 1 Stimulates Type X Collagen Promoter Via a Fos Family Protein," *Am. Soc. Bone & Min. Res.* 10:Suppl. 1, Abstract No. T345.

Harada et al. (1995), "Characterization of the Osteogenic Protein–1 Response Element in the Type X Collagen Promoter," *Mol. Biology of the Cell.* 6:Suppl., p. 393a, Abstract No. 2284.

Harada et al. (1995), "Characterization of the Osteogenic Protein–1 Response Region in the Type X Collagen Promoter," Abstract 124 *Bone* 17:590.

Harada et al. (1995), "Identification of an AP–1 Like Response Region For Osteogenic Protein–1 in Type X Collagen Promoter," Abstract Distributed at New York Academy Sciences, Molecular and Developmental Biology of Cartilage, Sep. 27–30, 1995.

Knutsen et al. (1995), "Regulation of Insulin–like Growth Factor System Components by Osteogenic Protein–1 in Human Bone Cells", *Endocrinology (US)* 136:857–865.

Merriman et al. (1995), "The tissue specific nuclear matrix protein NMP–2 is a member of the AML/CBF/PEBP2/ runt domain transcription factor family: interactions with the osteocalcin gene promoter," *Biochemistry* 34:13125–13132.

Orkin et al. (1995), "Report and Recommendations of the Panel to Assess the NIH Investment in Research on Gene Therapy," Dec. 7, 1995.

Sassone–Corsi (1995), "Signaling Pathways and c–fos Transcriptional Response—Links to Inherited Diseases," *N.E. J. Med.* 322:1576–1577.

Asahina et al. (1996), "Human Osteogenic Protein–1 Induces Chondroblastic, Osteoblastic, and/or Adipocytic Differentiation of Clonal Murine Target Cells," *Exp. Cell Res.* 222:38–47.

Galera et al. (1996), "C–Krox Binds to Several Sites in the Promoter of Both Mouse Type I Collagen Genes: Structure/Function Study and Developmental Expression Analysis," *J. Biol. Chem (US)* 271:21331–21339.

Harada et al. (1996), "Characterization of the Osteogenic Protein–1 Response Region in the Type X Collagen Promoter," Sixth Workshop On Cells and Cytokines In Bone and Cartilage, Davos, Switzerland, Jan. 7–10, 1996, *Bone* (New York) 17:124.

Lagna et al. (1996), "Partnership between DPC4 and SMAD proteins in TGF–β signalling pathways," *Nature* 383:832–836.

Massague, J. (1996), "TGFβ Signaling: Receptors, Transducers, and Mad Proteins," *Cell* 85:947–950.

Rossert, J.A. et al. (1996), "Identification of a minimal sequence of the mouse pro–alpha 1(I) collagen promoter that confers high–level osteoblast expression in transgenic mice and that binds a protein selectively present in osteoblasts," *Proc. Natl. Acad. Sci. USA* 93:1027–1031.

Solursh, M. et al. (1996), "Osteogenic Protein–1 is Required for Mammalian Eye Development," *Biochem. Biophys. Res. Comm.* 218:438–443.

```
                          SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 1067 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..1067
        (D) OTHER INFORMATION: /product= "MOUSE TYPE 10 COLLAGEN
            PROMOTER"

(xi) SEQUENCE DESCRIPTION: SEQ ID NO:1:

TCGATCCTAA AACACTTAAG GATATTTCTG TAAGGCTGTG AAAGAGAAAA CCAACTACTT      60

ACACGGATGG AGACCATGTT TATTTCTTTG GGAGAAAAGC CTAATTGGGA CGCTTCGAGA    120

TCCCTATAGG AAATTGCACC AGTAGTCAAC TGGATTTTTA AAAGGCAAAG CTTGAGGATT    180

TTTTTTTCCC TTTGAAATGA ATGTAGCAAA CTTATGTAAG CACGGAATAG GATTATTAGT    240

TAACAGTCTT TTCAATTATA TGGGAAAATG AAAACTAGGG GAGCGTCTAA GGCCACTTGC    300

TGACCTTTGT GCAGCTGTTA AGTAAAGAAA GTAAACCCTC CAGGGATACT GAACAGCCAA    360

CTGTCATAAG TCCAGGGTGT CTTGCACTTG CTGTGACAAG TTTAAAATAT TTAATATGAC    420

TATACCTGAA ATATTTAATG CTATCTTTTT CATGCACCAG CTTCTAAGAG CTTTCCCTAA    480

AATCCTGATA TGCAAAAGAA TATACCAATA TTTTCCCCCT TGCCCCTGGC GCTTGTCTCC    540

CAAGTTAGCA AACACTTAGG TAAGCGATTT TTACAGAACT TTTTTCCCTA ATAACTGAAG    600

GACTAACATG ATGATTTAGA TCTATATTCT CCCCAAAAGG CGTCTCATAT TTTTGTATAT    660

TACCAAATAT TTTCAGTCAA ATAACACAAG AATGTATTTT AAAAATAAAA AGGGTGAATC    720

ATCATTCCAT CATGAACCAA CATTGGACTC AGAACTCCTA AAAGGAAAAC AGAAAAAAAA    780

AAAAAATCAT GCACAGCCGA AGCTATTAAT ATATAATGGA GACAAAGAGT TTATTTTTCA    840

ATGAGAATAA CAAGGAAAAA AGCCTGATTT TGTACGCCTG CCCGTTAGGA CTTCCCACCA    900

TAATTAGTGC TTCTTGCCCC TGAGAGGAGG AGCTTCGGCT CAGGGGAACT TCATGCAATA    960

AGGGAAGAAA ACAGTATAAA TACTCCAGGG CAGCCGTGGG GAAGGCATTA TCCACTGCTC   1020
```

CTGGGCAGAG GAAGCCAGGA AAGCTGCCCC ACGCATCTCC CAGCACC                    1067

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..21
        (D) OTHER INFORMATION: /product= "AP1 SEQUENCE A"

(xi) SEQUENCE DESCRIPTION: SEQ ID NO:2:

CGCTTGATGA CTCAGCCGGA A                                                21

(2) INFORMATION FOR SEQ ID NO:3:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..10
        (D) OTHER INFORMATION: /product= "AP1 SEQUENCE A MUTATION"

(xi) SEQUENCE DESCRIPTION: SEQ ID NO:3:

TTCCTCATCA                                                             10

(2) INFORMATION FOR SEQ ID NO:4:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..25
        (D) OTHER INFORMATION: /note= "Conserved domain of human
            c-fos"

(xi) SEQUENCE DESCRIPTION: SEQ ID NO:4:

Lys Val Glu Gln Leu Ser Pro Glu Glu Glu Glu Lys Arg Arg Ile Arg
1               5                  10                  15

Arg Ile Arg Asn Lys Met Ala Ala Ala
            20                  25

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..15

(D) OTHER INFORMATION: /product= "AP-1 CONSENSUS SEQUENCE
                B"

(xi) SEQUENCE DESCRIPTION: SEQ ID NO:5:

GTGACTCAGC GCGGA                                                           15

(2) INFORMATION FOR SEQ ID NO:6:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1..11
            (D) OTHER INFORMATION: /product= "MEF-2 CONSENSUS"

(xi) SEQUENCE DESCRIPTION: SEQ ID NO:6:

CTAAAAATAA C                                                               11

(2) INFORMATION FOR SEQ ID NO:7:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1..11
            (D) OTHER INFORMATION: /product= "MEF-2 CONSENSUS MUTANT
                OLIGO"

(xi) SEQUENCE DESCRIPTION: SEQ ID NO:7:

TTAAACATAA A                                                               11

(2) INFORMATION FOR SEQ ID NO:8:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1..11
            (D) OTHER INFORMATION: /product= "MEF-2 MUTANT CONSENSUS"

(xi) SEQUENCE DESCRIPTION: SEQ ID NO:8:

CTAAACATAA C                                                               11

(2) INFORMATION FOR SEQ ID NO:9:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (xi) SEQUENCE DESCRIPTION: SEQ ID NO:9:

TTAAAAATAA A                                                               11

(2) INFORMATION FOR SEQ ID NO:10:

(i) SEQUENCE CHARACTERISTICS:

```
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:10:

TTAAAAATAA                                                                         10
```

METHODS AND COMPOSITIONS FOR IDENTIFYING MORPHOGEN ANALOGS

REFERENCE TO RELATED APPLICATIONS

The present application is a Continuation-in-Part application of co-pending U.S. Ser. No. 08/507,598, filed Jul. 26, 1995, the disclosure of which is herein incorporated by reference.

FIELD OF THE INVENTION

The present invention relates generally to methods and compositions for screening and identifying substances useful as morphogen analogs. In certain embodiments, the identified substances can be used to mimic a biological effect of morphogenic proteins such as osteogenic protein 1 (OP-1) on cellular gene expression and/or tissue-specific morphogenesis in mammals.

BACKGROUND OF THE INVENTION

Osteogenic Protein-1 of human origin (hOP-1), described in U.S. Pat. Nos. 5,011,691 and 5,266,683, and in Ozkaynak et al. (1990) EMBO J. 9: 2085–2093, recently has been appreciated to be competent to induce genuine tissue morphogenesis in mammals, including the endochondral morphogenesis of bone. It has further been appreciated that mouse OP-1 (see U.S. Pat. No. 5,266,683) and the Drosophila melanogaster gene product 60A, described in Wharton et al. (1991) Proc. Natl. Acad. Sci. USA 88:9214–9218 similarly induce true tissue morphogenesis in mammals. A recent study showed that mice lacking OP-1 display severe defects in kidney and eye development and skeletal abnormalities in the rib cage, skull and hind limbs (Dudley et al. (1995) Genes & Devel. 9:2795–2807 and Luo et al. (1995) Genes & Devel. 9: 2808–2820). Related proteins, including OP-2 (Ozkaynak (1992) J. Biol. Chem. 267:25220–25227 and U.S. Pat. No. 5,266,683); BMP5, BMP6 (Celeste et al. (1991) Proc. Natl. Acad. Sci. USA 87:9843–9847, Vgr-1 (Lyons et al. (1989) Proc. Natl. Acad. Sci. USA 86:4554–4558), and the like are similarly believed to be competent to induce true morphogenesis of mammalian tissue. As a result, significant effort has been devoted to characterizing and developing these and other functionally and structurally related proteins (collectively, morphogens) for use in the regenerative healing of injured or diseased mammalian tissues or organs. Particular effort has been devoted to developing morphogen-based therapeutics for the treatment of injured or diseased mammalian bone tissue, including for example, therapeutic compositions for inducing regenerative healing of bone defects such as fractures, as well as for preserving or restoring healthy metabolic properties in diseased bone tissue, e.g., osteopenic bone tissue. Complete descriptions of efforts to develop and characterize morphogen-based therapeutics for use in mammals, including humans, are set forth in pending U.S. patent application Ser. Nos. 08/404,113, 08/396,930, 08/445,467, 08/152,901, 08/432,883, 08/155,343, 08/260,675, 08/165,541, 08/174,605 and 07/971,091, the teachings of each of which are incorporated herein by reference.

Certain complications, however, presently are encountered during the production, formulation and use in vivo of therapeutic macromolecules, such as morphogen proteins. For example, such proteins are typically produced by fermentation or culture of suitable host cells. Any biological product produced from such host cells for use in humans presently must be shown to be essentially free of host cell contaminants, such as secreted or shed proteins, viral particles or degradation products thereof. Providing such assurance can add significantly to the cost and technical difficulty of commercial production of biological macromolecules. Furthermore, appropriate formulations must be developed for conferring commercially reasonable shelf life on the produced macromolecule, without significant loss of biological efficacy. An additional complicating factor arises when circumstances warrant an extended course of therapeutic treatment with the produced and formulated macromolecule: the treated mammal may develop an immunological response to the macromolecule, and any such response may interfere with effectiveness thereof. In extreme circumstances, treatment must be discontinued.

Accordingly, the need remains for the identification of therapeutically effective analogs of the aforesaid morphogens, particularly for analogs that are inexpensive to produce, are robust upon storage, and have a reduced propensity for eliciting undesirable side effects upon chronic or repeated administration to a mammal.

It is an object of the invention described herein to provide methods and compositions for identifying a morphogen analog, that is, for identifying a substance that mimics a morphogen biological effect in living cells or tissue. It is a further object of the present invention to provide an analog identified according to the present identification method. It is yet a further object to provide a therapeutic composition comprising an identified analog suitable for administration to a mammal in need thereof, such as a mammal afflicted with a metabolic bone disease, e.g., a disease characterized by osteopenia.

SUMMARY OF THE INVENTION

The present invention provides methods and compositions for identifying morphogen analogs. A morphogen analog of the present invention is a substance, preferably suitable for administration to a mammal in need thereof, that can induce a morphogen-mediated biological effect. That is, the analog of the present invention can reproduce a biological effect naturally induced in living mammalian cells or tissue by a morphogen. As used herein, the term "morphogen" embraces the class of proteins typified by human osteogenic protein 1 (hOP-1). hOP-1 and functionally equivalent morphogens are dimeric proteins that induce uncommitted cells of mammalian origin to undergo a cascade of cellular and molecular events that culminates in the formation of functional, differentiated mammalian tissues, e.g., bone, liver, nerve, tooth dentin, periodontal tissue, gastrointestinal tract lining tissue and the like. As described herein, morphogen analogs are identified by assessing whether candidate substances can mimic a morphogen such as OP-1 by inducing morphogen mediated expression of a reporter gene and/or by inducing a morphogen mediated biological effect. The present invention embraces substances identified according to the methods set forth herein as morphogen analogs. Further, the present invention provides for the production of commercially significant quantities of identified morphogen analogs. Still further, the invention provides for the manufacture and use of DNA comprising a morphogen-responsive transcription activating element. The present DNA can be used to render the expression of a gene of interest, e.g., a reporter gene encoding a detectable gene product, inducible by OP-1 or a functionally equivalent morphogen or analog thereof. Yet further, the present DNA can be used in the manufacture of a cell for the in vitro or in vivo morphogen or analog inducible expression of a gene product of interest. Still further, the present DNA and intracellular proteins that bind thereto can be used to identify cells and/or tissue which are morphogen-responsive, as well as probes to monitor cell differentiation and/or tissue morphogenesis, e.g., chondrocyte differentiation.

Accordingly, in one aspect, the instant invention features an identification method in which a test cell is exposed to at least one candidate substance suspected of having activity as a morphogen analog. The test cell comprises DNA defining an OP-1 responsive transcription activating element, and, in operative association therewith, a reporter gene encoding a detectable gene product. Thus, when the DNA is present in an OP-1 responsive cell (e.g., any cell that manifests an OP-1 mediated biological effect), the DNA serves to induce transcription of the reporter gene when the OP-1 responsive cell is exposed to OP-1. The present method further comprises the step of detecting expression of the detectable gene product following exposure of the test cell to one or more candidate substances. Expression of the detectable gene product indicates that the candidate substance is competent to induce an OP-1 mediated biological effect. An OP-1 mediated biological effect of particular interest herein comprises the transcriptional activation of OP-1 responsive genes, that is, genes with which the present activating element is naturally in operative association. In a related embodiment useful for identification of responsive cells and/or tissue, binding of certain intracellular substances to the transcription activation element following exposure to a morphogen or analog thereof is a measure of responsiveness. In certain preferred embodiments, DNA binding occurs within 2–12 hours of morphogen treatment, thereby providing an early indicator of morphogen responsiveness as well as an early indicator of the ability to mimic a morphogen. Such intracellular substances are discussed below.

In certain embodiments, the present method further comprises the steps of contacting an OP-1 responsive cell with a putative morphogen analog identified as described above and detecting whether the analog can induce a biological effect known to be mediated naturally by OP-1 in the OP-1 responsive cell. If desired, this confirming step can be carried out concurrently with the initial identification steps. In certain specific embodiments, the test cell is an OP-1 responsive cell.

In other embodiments, the present method further comprises the steps of administering the putative morphogen analog identified as described above to a morphogenically permissive, tissue-specific locus in a mammal and detecting whether the analog can induce tissue-specific morphogenesis at the locus. This confirming step advantageously indicates whether the analog will induce tissue-specific morphogenesis in vivo.

In a related aspect, the present invention provides one or more substantially pure substances competent to bind to one or more portions of the above-mentioned OP-1 responsive transcription activating element, such that the substance or substances, when so bound, modulate expression of a gene in operative association with the aforesaid transcription activating element. The transcription activating element comprises at least two distinguishable sites, one of which comprises an A/T rich nucleotide sequence which shares sequence similarity to the consensus sequence for monocyte enhancer factor 2 (MEF-2), referred to herein as an MEF-2 or MEF-2-like sequence, known to play an important role in myoblast differentiation (Olson et al. (1995) *Devel. Biol.* 172:2–14) and to be a member of the MADS box family of transcription factors. Another site within the transcription activating element, which is adjacent to the A/T rich sequence, comprises a nucleotide sequence which shares sequence similarity to the AP-1 consensus sequence and is referred to herein as an AP-1 or AP-1 like sequence. Each site is capable of binding at least one nuclear factor which are distinguishable one from the other. These nuclear factors are referred to herein as "expression activators".

Accordingly, it will be appreciated that the present invention provides a method for assessing whether a sample such as a cell-free lysate or extract of biological origin, comprises one or more of these expression activators. In this method, the sample is contacted with the above-described DNA, and binding of one or more expression activators to the DNA is subsequently detected according to art known methods. Such a method permits the skilled artisan to probe different tissues and screen for morphogen responsive tissue types. Such a method further permits identification of morphogen analogs which facilitate binding of nuclear components to the above-described DNA. Furthermore, this identification method can be routinely adapted for use as an affinity purification method to obtain purified preparations of these and other expression activators. As disclosed herein, these expression activators are novel intracellular protein that are members of the fos or MADS box families of DNA binding proteins.

As a result of the present analog identification method, the invention provides for the production of therapeutic-grade, commercially-significant quantities of an identified morphogen analog. The invention further provides for production of a derivative of the morphogen analog in which any undesirable properties of the initially-identified analog, such as in vivo toxicity or tendency to degrade upon storage, are mitigated. Thus, a morphogen analog or functionally equivalent derivative thereof can be formulated in a therapeutic composition suitable for administration to a mammal in need thereof. Preferably, the therapeutic composition is suitable for administration to a primate, such as a human. Mammals in need of the morphogen analog identified as described herein can be afflicted with any disease or condition for which elicitation of a morphogenic biological effect will provide an improvement in the mammals' health or clinical status, including the stabilization of a deteriorative condition. For example, the mammal can be afflicted with a metabolic bone disease, e.g., a disease characterized by osteopenia. OP-1, related morphogens and analogs thereof are anticipated to beneficially alter the metabolic balance of osteopenic bone tissue such that the metabolic properties of healthy adult bone tissue are restored therein. Alternatively the mammal can be afflicted with ischemic, ulcerative or inflammatory tissue damage, or with injury or deterioration of a morphogen-responsive tissue such as bone, liver, kidney, nerve, gastrointestinal tract lining, tooth dentin, periodontal tissue and the like. Further, the therapeutic composition can be suitable for the treatment or preservation ex vivo of mammalian tissue or cells, e.g., for purposes of organ or tissue transplantation.

Another aspect of the present invention provides a cell for the inducible expression of a morphogen. The cell comprises a first DNA encoding the morphogen and a second DNA in transcriptionally operative association therewith and comprising the above-described morphogen responsive transcription activating element. The cell further comprises cellular means for producing one or more intracellular substances that bind with defined portions of the second DNA so as to stimulate expression of the morphogen encoded by the first when the cell is contacted with an extracellular inducing agent. Thus, for example, the cell comprises means for producing one or more of the expression activators of the present invention. Of course, according to the inventive principles set forth herein, the cell of the present invention can comprise a first DNA encoding any desired gene product, the expression of which is advantageously induced by a morphogen, particularly OP-1, or by a morphogen analog of the present invention. In certain embodiments, the first DNA comprises a reporter gene encoding a detectable gene product. Cells comprising such a first DNA are suitable for use in the above-described method for identifying morphogen analogs.

In other embodiments, the first DNA comprises a gene encoding a gene product having biological activity, e.g., an enzyme, growth factor, lymphokine, cytokine, blood or serum protein, clotting factor, or the like. Thus, the first DNA can encode a polypeptide naturally produced by kidney, bone, liver, nerve, pancreatic, adrenal or other mammalian body tissue. Cells comprising such a first DNA are suitable for the inducible production, either in vitro or in vivo, of the biologically active encoded gene product.

Accordingly, in another aspect, the invention provides methods for inducing expression, including autocrine expression, of a gene product such as a morphogen encoded by said first DNA. The present methods involve providing one of the above-described cells and contacting the cell with an extracellular inducing agent, such as OP-1, or an analog thereof, under conditions sufficient to induce expression of the gene present in said first DNA. The induced expression is referred to herein as autocrine expression when the extracellular inducing agent is the same substance as that encoded by the first DNA, such that an initial dose of the extracellular inducing agent triggers sustained expression of the first DNA in a manner similar to naturally occurring autocrine expression or positive feedback expression in biological systems. Certain embodiments of the present invention further involve the additional step of providing the above-described cell to a mammal for in vivo production of the product encoded by the first DNA. Advantageously, the above-described contacting step can be carried out by administering the extracellular inducing agent to the mammal in which the cell is implanted. The present invention accordingly provides novel methods for administering a morphogen or another gene product having biological activity, to a mammal in need thereof. The present methods offer particular advantages where the mammal has a long-term need for the morphogen or other gene product, e.g. wherein the mammal has a metabolic bone disease, such as, for example, osteopenia. Alternatively, the present methods offer advantages where the mammal suffers from a clinically acute loss of natural tissue function, such that augmented tissue function must be supplied for a sufficient period of time for healing or regeneration of damaged natural tissue to occur. The present cells can, for example, supply a product normally produced by kidney or liver tissue to a mammal afflicted with kidney or liver failure, optionally for which a regenerating amount of a morphogen such as OP-1 is being administered concurrently to the mammal.

It will therefore be apparent that the present invention features DNA defining a morphogen responsive transcription activating element or a portion thereof sufficient for the binding of one or more intracellular expression activators. As indicated above, a currently preferred morphogen is OP-1. The present DNA is in operative association which a cloning site suitable for insertion of a gene, such as a reporter encoding a detectable gene product or a therapeutic gene encoding a product having biological activity. When the reporter gene is inserted at the cloning site, the reporter gene is operatively associated with the morphogen-responsive transcription activating element such that the detectable gene product is produced when present in a cell of the present invention and the cell is contacted with an extracellular inducing agent, such as a morphogen. That is, the DNA described herein serves to induce transcription of the inserted gene. Certain currently preferred embodiments of the present DNA comprise an OP-1 responsive transcription activating element that occurs naturally at least in the promoter region of the mammalian type X collagen gene. Thus, in one particularly preferred embodiment, the sequence of the present DNA comprises nucleotides 699–731 of SEQ. ID No. 1, as disclosed herein. The DNA of the present invention advantageously can be contained in a suitable receptacle to provide a kit for facilitating the practice of any of the above-described methods. Optionally, the present kits further contain a morphogen and/or a morphogen analog identified according to the present invention.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which.

DETAILED DESCRIPTION OF PREFERRED EMBODIMENTS

Figure 1:
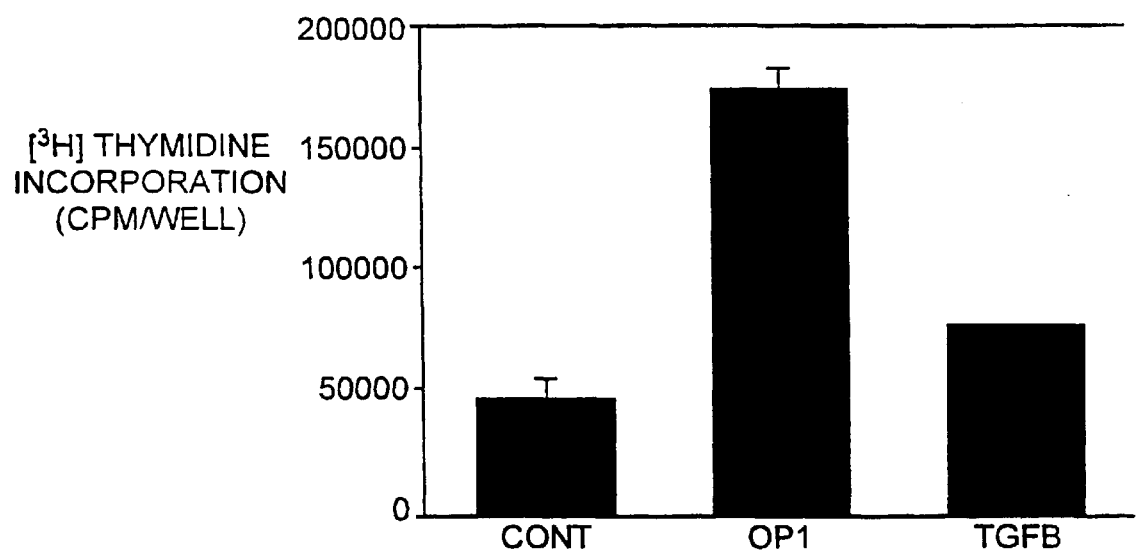
FIG. 1 is a bar graph illustrating the effects of OP-1 and TGFβ on proliferation of C5.18 fetal calvaria cells using $^3$H-thymidine incorporation as a measure of mitogenesis.

The invention described herein capitalizes on the discovery that morphogens, particularly OP-1, can affect expression of certain genes, present naturally in the genome of mammalian cells. That is, stimulation of mammalian cells with a morphogen such as OP-1 induces a spectrum of biological effects, including but not limited to the transcriptional activation of selected cellular genes. The promoter region of at least one such gene has been analyzed and, as disclosed herein, found to comprise a morphogen responsive transcription activating element. Following contact of the cell with the exemplary OP-1, the transcription activating element specifically induces transcription at least of a gene (s) which is situated downstream of and operatively associated with the element. This specific transcriptional activation involves binding of one or more intracellular substances ("expression activators") to the OP-1 responsive transcription activating element. These intracellular substances bind with portions of the preferred responsive transcription activating element naturally disposed within the promoter region of the mammalian type X collagen gene, at a 5' region of the element which is A/T rich resembling an MEF-2 concensus sequence, and at an adjacent 3' region thereof resembling an AP-1 binding site sequence. It is shown herein that deletion or mutation of the morphogen responsive transcription activating element results in loss of OP-1 responsive transcriptional activation of the downstream gene(s) operatively associated with the element.

The present methods and compositions accordingly exploit the morphogen responsive properties of the newly-discovered transcription activating element. Generally, the methods and compositions of the present invention provide the skilled artisan with the analytical tools and technical know-how sufficient to identify substances (morphogen analogs) that can mimic a biological effect induced by a morphogen such as OP-1. Guidance provided herein accordingly will facilitate evaluation of a variety of diverse substances for morphogen analog properties, thereby broadening the spectrum of potential therapeutic candidates for amelioration and/or treatment of diseases, injuries and deteriorative disorders, such as metabolic bone diseases, for which morphogens are anticipated to provide clinical benefit.

Morphogens, as defined herein, induce or re-induce mammalian cells, particularly uncommitted progenitor cells, to undergo a fully integrated developmental cascade of biological and molecular events that culminate in the morphogenesis of fully differentiated, functional tissue of a type appropriate to the context or local biological environment in which morphogenesis is induced, including any vascularization, connective tissue formation, enervation and the like characteristic of tissue naturally-occurring in such a context. For example, if cells are stimulated by OP-1 in the context of nerve, bone or liver tissue, the resulting cascade of morphogenesis culminates in the formation of new or regenerative differentiated tissue appropriate to the selected local environment. Morphogenesis therefore differs significantly from simple reparative healing processes in which scar tissue (e.g., fibrous connective tissue) is formed and fills a lesion or other defect in differentiated, functional tissue.

Further, morphogenesis as contemplated herein occurs in a "permissive environment" by which is meant a local environment that does not stifle or suppress morphogenesis (e.g., regeneration or regenerative healing). Permissive environments exist, e.g., in embryonic tissue or in wounded or diseased tissue, including tissue subjected to surgical intervention. Often, a permissive environment comprises a suitable matrix or substratum to which cells undergoing differentiation can anchor. Exemplary matrices comprise tissue-specific structural components, e.g., collagen or glycosaminoglycans of the same types as occur naturally in the desired tissue. Other components of a permissive environment typically include signals, e.g., cell surface markers or extracellular secreted substances, that direct the tissue specificity of differentiation.

Morphogens are structurally and functionally related to OP-1 and thus include the family of dimeric proteins naturally produced by eukaryotic cells and having tissue-specific morphogenic activity, e.g., activity in inducing endochondral bone morphogenesis, when implanted in a mammal. Morphogens accordingly comprise a distinct subclass of the super family of TGFβ-like proteins. A morphogen as isolated from natural sources in mature, biologically active form is a glycosylated dimer typically having an apparent molecular weight of about 30–36 kDa as determined by SDS-PAGE. When reduced, the 30 kDa protein gives rise to two glycosylated peptide subunits having apparent molecular weights of about 16 kDa and 18 kDa. The reduced polypeptides themselves have no detectable morphogenic activity. Glycosylation, however, is not required for biological activity. The unglycosylated protein has an apparent molecular weight of about 27 kDa. When reduced, the 27 kDa protein gives rise to two unglycosylated polypeptides having molecular weights of about 14 kDa to 16 kDa. The polypeptides which together form the biologically active dimer comprise at least six, preferably at least seven, positionally conserved cysteine residues as set forth in U.S. Ser. No. 08/396,930, the teachings of which have been incorporated herein by reference.

As stated above, the representative morphogen, for purposes of the present invention, comprises an OP-1 or an OP-1-related polypeptide. Sequences of useful OP-1 polypeptides are recited in U.S. Pat. Nos. 5,011,691; 5,018,753 and 5,266,683; in Ozkaynak et al. (1990) *EMBO J* 9:2085–2093; and Sampath et al. (1993) *Proc. Natl. Acad. Sci. USA* 90: 6004–6008. Additional useful sequences occur in the C-terminal domains of DPP (from Drosophila), Vgl (from Xenopus), 60A (from Drosophila, see Wharton et al. (1991), *Proc. Natl. Acad. Sci. USA* 88:9214–9218), Vgr-1 (from mouse), the OP-1 and OP-2 proteins, (see U.S. Pat. No. 5,011,691 by Oppermann et al.), as well as the proteins referred to as BMP2, BMP3, BMP4 (see WO88/00205, U.S. Pat. No. 5,013,649 and WO91/18098), BMP5 and BMP6 (see WO90/11366, PCT/US90/01630) and BMP8 and 9. Each of the foregoing polypeptides, when oxidized and dimerized, is useful as a morphogen herein. Further, this family of morphogenic proteins includes longer forms of a given protein, as well as phylogenetic, e.g., species and allelic variants and biosynthetic mutants thereof, including addition and deletion mutants and variants, such as those which may alter the conserved C-terminal cysteine skeleton, provided that the alteration still allows the protein to form a dimeric species having a conformation capable of inducing morphogenesis, e.g., endochondral bone formation when implanted in a mammal in conjunction with a matrix permissive of bone morphogenesis. In addition, morphogens useful in this invention may include forms having varying glycosylation patterns and varying N-termini, may be naturally occurring or biosynthetically derived, and may be produced by expression of recombinant DNA in prokaryotic or eukaryote host cells according to established techniques. The proteins are active either as homodimers or heterodimers.

Morphogens generally induce all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells. The term "progenitor cells" includes uncommitted cells, preferably of mammalian origin, that are competent to differentiate into one or more specific types of differentiated cells, depending on their genomic repertoire and the tissue specificity of the permissive environment in which morphogenesis is induced. Preferably, morphogenesis culminates in the formation of differentiated tissue having structural and function properties of a tissue that occurs naturally in the body of a mammal.

Morphogens further can delay or mitigate the onset of senescence- or quiescence-associated loss of phenotype and/or tissue function. Morphogens still further can stimulate phenotypic expression of differentiated cells, including expression of metabolic and/or functional, e.g., secretory, properties thereof. In addition, morphogens can induce redifferentiation of transformed cells under appropriate environmental conditions. As noted above, morphogens that induce proliferation and differentiation at least of mammalian bone progenitor cells, and/or support the formation, growth, maintenance and functional properties of mammalian endochondral bone tissue, are of particular interest herein.

Accordingly, a morphogen analog is a substance that mimics a biological effect induced and/or mediated by a morphogen, such as OP-1. Any substance having such mimetic properties, regardless of the chemical or biochemical nature thereof, can be used as a morphogen analog herein. The present morphogen analog can be a simple or complex substance produced by a living system or through chemical or biochemical synthetic techniques. It can be a substance that occurs in nature or a novel substance, e.g., prepared according to principles of rational drug design. It can be a substance that structurally resembles a solvent-exposed morphogen surface epitope implicated in receptor interactions, a substance that otherwise stimulates a morphogen receptor displayed on the surface of a morphogen responsive cell, or a cell-membrane permeate substance that interacts with an intracellular component of the signal transduction machinery of a morphogen responsive cell.

Thus, for example and without being limited hereto, one type of morphogen analog of the present invention can be prepared through judicious application of the principles of biosynthetic antibody binding site (BABS) technology as set forth in U.S. Pat. Nos. 5,132,405, 5,091,513 and 5,258,498, the teachings of which are incorporated herein by reference. BABS analog constructs can be prepared from antibodies, preferably produced by hybridoma cells, that bind specifically to a morphogen cell surface receptor. Alternatively, BABS analysis can be prepared from anti-idiotypic antibodies specifically reactive with the antigen binding site of an antibody that blocks morphogen biological activity. Vukicevic et al. (1994) Biochem. Biophys. Res. Comm. 198:693–700 teaches the preparation of OP-1 specific monoclonal antibodies. Skilled artisans will appreciate that such antibodies can be used as immunogens in the routine preparation of anti-idiotypic antibodies from which BABS analogs of the present invention can be prepared.

A structurally distinct class of morphogen analogs, again set forth herein for illustration and not for limitation, can be prepared through judicious application of the principles of directed molecular evolution as set forth in Tuerk et al. (1990) Science 249:505–510, Famulok et al. (1992) Angew. Chem. Intl. Ed. Engl. 31:979–988 and Bock et al. (1992) Nature 355:564–556, the teachings of each of which are incorporated by reference herein. The directed molecular evolution process involves isolation of a nucleic acid molecule, typically an RNA, that binds with high affinity to a selected ligand such as a protein. Such a nucleic acid molecule is referred to in the art as an "aptamer." The desired aptamer is initially present in a random pool of nucleic acid molecules, and is isolated by performing several rounds of ligand-affinity based chromatography alternating with PCR-based amplification of ligand-binding nucleic acids. Bock et al. (1992), above, have demonstrated the preparations of aptamers, suitable for in vivo use in mammals, that specifically inhibit the blood clot promoting factor, thrombin.

Yet another structurally distinct class of morphogen analogs can be prepared by selecting appropriate members of a random peptide library (Scott et al. (1990) Science 249:386–390) or a combinatorially synthesized random library of organic or inorganic compounds (Needels et al. (1993) Proc. Natl. Acad. Sci. USA 90:10700–10704; Ohlmeyer et al. (1993) Proc. Natl. Acad. Sci. USA 90:10922–10926). Skilled artisans will appreciate that the foregoing and other related technologies, taken together with long-established principles of screening biologically-produced substances, offer a wide array of candidate substances for screening for morphogen analog activity.

Thus, a naturally-sourced OP-1 or morphogen analog can comprise a polypeptide, polynucleotide, carbohydrate, lipid, amino acid, nucleic acid, sugar, fatty acid, steroid, or a derivative of any one of the aforementioned compounds. It can be an intermediate or end product of metabolism of a eukaryotic or prokaryotic cell. Alternatively, the analog can be a biological response modifier or a toxin.

Thus, a morphogen analog identified according to the method of the present invention is a substance that mimics a morphogen by inducing at least one "morphogen-mediated biological effect" in a morphogen-responsive cell or tissue. The effect can be any biological effect resulting from exposure to or contact with a morphogen, including but not limited to the induction of tissue-specific morphogenesis. Morphogen-mediated biological effects include cellular and molecular responses to morphogen exposure, e.g., as described in U.S. Ser. Nos. 08/115,914, 08/155,343, 08/260, 675, 08/165,541 and 08/174,605, the disclosures of which have been incorporated herein by reference. It will accordingly be appreciated that an "OP-1 mediated biological effect" is any biological effect resulting from exposure to or contact of morphogen-responsive cells or tissue with OP-1, whether in vitro or in vivo. A morphogen mediated biological effect of particular interest herein includes OP-1 stimulation of the expression of one or more specific gene(s), including stimulation of the binding of one or more intracellular substances to DNA expression regulation elements. Other morphogen mediated biological effects include stimulation of cellular proliferation, cellular differentiation, maintenance of a differentiated phenotype, and, under the appropriate circumstances, induction of redifferentiation. Further preferred morphogen mediated biological effects are molecular or biochemical effects associated with tissue-specific morphogenesis, e.g., endochondral bone formation or nerve regeneration.

Specific OP-1 mediated biological effects associated with endochondral bone formation include induction of mitogenesis and phenotypic markers for chondrocyte and osteoblast differentiation in fetal rat calvaria cells. Useful induced phenotypic markers include types I, II and X collagen; alkaline phosphatase; and osteocalcin. Thus, a candidate compound identified as an OP-1 analog using the methods and compositions of the instant invention can mimic OP-1 by inducing at least one of the foregoing biological effects.

Accordingly, in a first aspect, the present invention features a method of identifying a morphogen analog that induces a morphogen mediated biological effect. This method involves the step of providing a test cell comprising DNA defining an OP-1 responsive transcription activating element, and, in operative association therewith, a reporter gene encoding a detectable gene product. The present OP-1 (or morphogen) responsive transcription activating element is a cis-acting DNA element, a preferred sequence of which is disclosed herein, that modulates expression of a downstream gene in an OP-1 (or morphogen) responsive cell. The OP-1 responsive transcription activating element can be located between about 100–600 base pairs, preferably about 250–400 base pairs, upstream of the gene's transcriptional initiation site. Regardless of its exact relative location, the OP-1 responsive element is in operative association with the downstream gene if its activation stimulates transcription thereof. That is, when OP-1 is administered to an OP-1 responsive cell and thereby induces an intracellular cascade of biological responses, one such response comprises induction of expression of this downstream gene. Evidence presented herein indicates that this effect is accomplished via the binding of one or more intracellular substances ("expression activators") to defined portions of the OP-1 responsive transcription activating element.

The present test cell is any cell comprising DNA defining an OP-1 responsive transcription activating element operatively associated with a reporter gene encoding a detectable gene product. Such DNA can occur naturally in a test cell or can be a transfected DNA. Thus, the test cell can optionally be an OP-1 responsive cell. An "OP-1 responsive cell" is any cell that manifests an intracellular OP-1 mediated biological effect. A morphogen responsive cell is herein defined similarly. The induced intracellular biological effect is characteristic of morphogenic biological activity, such as activation of a second messenger cascade of events involving for example, cyclic nucleotides, diacylglycerol, and/or and other indicators of intracellular signal transduction such as activation or suppression of gene expression, including induction of mRNA resulting from gene transcription and/or induction of protein synthesis resulting from translation of mRNA transcripts indicative of tissue morphogenesis. Exemplary OP-1 responsive cells are preferably of mammalian origin and include, but are not limited to, osteogenic progenitor cells; calvaria-derived cells; osteoblasts; osteoclasts; osteosarcoma cells and cells of hepatic or neural origin. Any such OP-1 or morphogen responsive cell can be a suitable test cell for assessing whether a candidate substance induced is a morphogen analog.

The present identification method is carried out by exposing a test cell to at least one candidate substance; and, detecting whether such exposure induces expression of the detectable gene product that is in operative association with the OP-1 responsive transcription activating element of the present invention. Expression of this gene product indicates that the candidate substance can induce an OP-1 mediated biological effect. Skilled artisans can, in light of guidance provided herein, construct a test cell with a responsive element from an OP-1 responsive cell and a reporter gene of choice, using recombinant vectors and transfection techniques well-known in the art. There are numerous well-known reporter genes useful herein. These include, for example, chloramphenicol acetyltransferase (CAT), luciferase, human growth hormone (hGH), beta-galactosidase, and assay systems and reagents which are available through commercial sources. As will be appreciated by skilled artisans, the listed reporter genes represent only a few of the possible reporter genes that can be used herein. Examples of such reporter genes can be found in Ausubel et al., Eds., *Current Protocols in Molecular Biology,* John Wiley & Sons, New York, (1989). Broadly, any gene that encodes a detectable product, e.g., any product having detectable enzymatic activity or against which a specific antibody can be raised, can be used as a reporter gene in the present identification method.

A currently preferred reporter gene system is the firefly luciferase reporter system. (Gould, S. J., and Subramani, S. (1988) *Anal. Biochem.,* 7:404–408 incorporated herein by reference). The luciferase assay is fast and sensitive. In this assay system, a lysate of the test cell is prepared and combined with ATP and the substrate luciferin. The encoded enzyme luciferase catalyzes a rapid, ATP dependent oxidation of the substrate to generate a light-emitting product. The total light output is measured and is proportional to the amount of luciferase present over a wide range of enzyme concentrations.

CAT is another frequently used reporter gene system; a major advantage of this system is that it has been an extensively validated and is widely accepted as a measure of promoter activity. (Gorman C. M., Moffat, L. F., and Howard, B. H. (1982) *Mol. Cell. Biol.,* 2: 1044–1051 incorporated herein by reference). In this system, test cells are transfected with CAT expression vectors and incubated with the candidate substance within 2–3 days of the initial transfection. Thereafter, cell extracts are prepared. The extracts are incubated with acetyl CoA and radioactive chloramphenicol. Following the incubation, acetylated chloramphenicol is separated from nonacetylated form by thin layer chromatography. In this assay, the degree of acetylation reflects the CAT gene activity with the particular promoter.

Another suitable reporter gene system is based on immunologic detection of hGH. This system is also quick and easy to use. (Selden, R., Burke-Howie, K. Rowe, M. E., Goodman, H. M., and Moore, D. D. (1986), *Mol. Cell, Biol.,* 6:3173–3179 incorporated herein by reference). The hGH system is advantageous in that the expressed hGH polypeptide is assayed in the media, rather than in a cell extract. Thus, this system does not require the destruction of the test cells. It will be appreciated that the principle of this reporter gene system is not limited to hGH but rather adapted for use with any polypeptide for which an antibody of acceptable specificity is available or can be prepared.

Regardless of the reporter gene system used, the candidate substance is exposed to the test cell for a sufficient period of time and under sufficient cell culture conditions for the morphogen mediated biological effect (production of the detectable gene product) to be induced. For example, using the presently preferred OP-1 responsive transcription activating element and fetal rat calvaria cells as described in the Examples below, one OP-1 mediated biological effect is induced at least as early as 24 hrs. after exposure to OP-1. Thus, preferred candidate substances diluted to appropriate, non-toxic, biologically relevant concentrations and exposed to the rat calvaria test cell of the present examples, are anticipated to induce detectable gene product at least as early as about 16 hrs., more preferably 12 hrs., with optimal levels detectable preferably about 24 hrs. yet prior to about 36 hr of exposure to said cell thereto. Suitable cell culture conditions for the exposure step will vary depending on the precise nature of the test cell and can be optimized by the skilled artisan through no more than routine experimentation.

Additionally, the skilled artisan can practice certain other embodiments of the instant method once a putative morphogen analog is identified using the above-described identification method. That is, confirmatory screening of the putative analog can involve the additional steps of contacting an OP-1 responsive cell therewith and detecting induction of a biological effect known to be mediated by OP-1 in the OP-1 responsive cell. Induction of the biological effect further confirms the substance's identity as a potential OP-1 (or morphogen) analog. Skilled artisans will appreciate that, under certain circumstances, detecting expression of the reporter gene and detecting induction of the biological effect can occur concurrently. Similarly, the test cell can itself be OP-1 responsive.

Certain other embodiments of the instant method can permit further confirmatory screening of the above-identified putative analog. Such optional methods involve the additional steps of providing the putative analog to a morphogenically permissive, tissue-specific locus in a mammal and detecting induction of tissue-specific morphogenesis at the locus, the induction being indicative of the analog's ability to induce tissue-specific morphogenesis in a mammal. This embodiment allows the skilled artisan to confirm with reasonable certainty that a promising substance indeed has utility as an OP-1 or morphogen analog.

A morphogen analog identified as described above accordingly can be produced in therapeutic-grade, commercially-significant quantities and formulated for administration to a mammal, preferably to humans for therapeutic effect. If desired, e.g., to reduce toxicity, improve shelf life or biological potency, a derivative of the identified morphogen analog having substantially the same morphogen-mimetic properties thereof also can be produced.

Any appropriate method can be used for production of a particular morphogen analog. For example, such methods can include, but are not limited to, methods of biological production, such as from a host cell or synthetic production of a peptide. Additionally, methods can include non-biological chemical synthesis. Still other methods can include production by fermentation or cell culture using a cell producing the analog compound. Naturally-sourced analogs can be, for example, expressed from intact or truncated genomic or cDNA, or from synthetic DNAs in prokaryotic or eukaryote host cells, and purified, cleaved, refolded and oxidized as necessary to form active molecules. Useful host cells include prokaryotes including *E. coli* and *B. subtilis,* and eukaryotic cells including mammalian cells such a fibroblast 3T3 cells, CHO, COS, melanoma or BSC cells, Hela and other human cells, the insect/baculovirus system, as well as yeast and other microbial host cell systems. Alternatively, proteins can be chemically synthesized using standard chemical peptide synthesis methodologies well described in the art and commercially available. Similarly, non-peptide molecules can be chemically synthesized using standard chemical protocols.

In another aspect, the present invention features DNA for inducing a morphogen and/or OP-1 mediated biological effect. For example, the present DNA defines an OP-1 responsive transcription activating element such that the DNA, when present in an OP-1 responsive cell contacted with OP-1, serves to induce transcription of a gene located downstream and in operative association with the aforesaid element. Specifically, in one currently preferred embodiment, the sequence of DNA defining the OP-1 responsive transcription activating element is that depicted by a core sequence comprising nucleotides 699–731 of SEQ. ID No. 1 described herein. In another currently preferred embodiment, the preferred DNA is depicted by nucleotides 682–731 of SEQ. ID No. 1 which includes nucleotides 682–698 of SEQ. ID No. 1 flanking an A/T rich region in the core sequence at the 5' end and nucleotides 725–731 of SEQ. ID. No. 1 flanking an AP-1 like site in the core sequence at the 3' end. In yet another embodiment, a preferred DNA is depicted by nucleotides 682–761 of SEQ. ID No. 1 which includes nucleotides 682–698 of SEQ. ID NO. 1 flanking the core sequence at the 5' end and nucleotides 732–761 of SEQ. ID No. 1 flanking the core sequence at the 3' end.

In a currently preferred embodiment, an A/T rich sequence (nucleotides 699–711 of SEQ. ID No 1) is 5' and adjacent to an AP-1 like sequence (nucleotides 715–724 of SEQ. ID NO.1). Currently, a spacer region disposed between said A/T rich and AP-1 like sequences is preferably, but not limited to, a sequence that comprises the sequence GGG (712–714 of SEQ. ID No. 1). Additionally, the instant invention contemplates DNA which hybridizes specifically with any one of the above-described DNA sequences. As used herein, "hybridizes specifically" means hybridizes under conditions that are defined in the art as low stringency conditions. An exemplary set of conditions is thus: hybridization in 30% formamide, 1M NaCl, 50 mM Tris (pH 7.5), 0.5% SDS, 10% Dextran Sulfate, 1X Denhardt's Solution, and 1 mg/ml denatured salmon sperm DNA for a total of 20 hours at 42° C., followed by washing at room temperature once in 2X SSC/0.1% SDS, and then twice at 55° C. in 1X SSC/0.1% SDS for fifteen minutes each. See, e.g., U.S. Pat. No. 5,359,047 the disclosure of which is herein incorporated by reference.

Thus, the currently preferred OP-1 responsive transcription activating element comprises a core region of nucleotides at positions 699–731 of SEQ. ID No. 1. This particular core sequence is expected to hybridize specifically at least with a DNA binding site sequence resembling an AP-1 DNA consensus sequence A previously described in the art (SEQ. ID No. 2; see also Lee et al. (1989) *Cell* 49: 741–752). Furthermore, the 5' end of this core sequence comprises an A/T rich sequence (nucleotides 699–711 of SEQ. ID No. 1) which is analogous to that of an MEF-2 consensus sequence (Seq. ID No. 6) (Yu et al. (1992) *Genes Dev.* 6:1783–1798) while the 3' end (nucleotides 715–724 of SEQ. ID No. 1) contains a sequence resembling an AP-1 binding site. Accordingly, the present invention contemplates an isolated DNA sequence defining a morphogen-responsive transcription activating element comprising: nucleotides 699–731, 682–731, 682–761; species and allelic variants thereof; DNA which hybridizes to the strand complementary to the foregoing and is morphogen-responsive under native conditions; and biosynthetic variants of all the foregoing embodiments. Additionally, a feature of these isolated DNA sequences is an MEF-2 binding site sequence (or AT rich equivalent thereof) adjacent an AP-1 binding site sequence (or equivalent thereof).

Thus, in another aspect, the present invention provides one or more substantially pure substances competent to bind to and/or interact with the above-mentioned OP-1 responsive transcription activating element and isolated DNA's, or portions thereof, such that the substances have the property of modulating expression of a gene encoding a gene product when the above-described DNA's are in operative association therewith and one or more of the substances are bound thereto. In a currently preferred embodiment, these substantially pure substances, referred to herein as expression activators, bind at least to the core sequence of the currently preferred responsive element, e.g., to nucleotides 699–731 of SEQ. ID No.1, thereby modulating expression of a downstream gene encoding a gene product operatively associated with the responsive element. As discussed earlier and exemplified herein below, a currently preferred substance for binding to the AP-1 like site (nucleotides 715–724 of SEQ. ID No. 1) is a proteinaceous intracellular substance having general immunological properties of a fos family protein. Fos family proteins have been implicated in chondrogenesis and osteogenesis and c-fos and fra-2 are highly expressed in bone and cartilage during development (Dony and Gruss (1987), *Nature* 328:711–714; Sandberg et al. (1988), *Development*, 102:461–470; Carrasco and Bravo (1995), *Oncogene,* 10:1069–1079). Expression of c-fos in osteoblasts, osteocytes, chondrocytes or in bone is induced by osteogenic factors, mechanical stress, or fracture repair. Thus, in one currently preferred embodiment, the AP-1 like binding substance comprises a polypeptide having an amino acid sequence which shares immunoreactivity with the conserved domain of human c-fos; specifically, with amino acid residues 128–152 of human c-fos protein as depicted by amino acid residues 1–25 in SEQ. ID No. 4. In particular, one exemplary AP-1 like binding substance comprises an epitope which is bound by the antibody designated "c-fos (K-25)" available as Catalog No. sc-253 from Santa Cruz Biotechnology, Inc., Santa Cruz, Calif. This antibody is a rabbit affinity-purified polyclonal antibody raised against a peptide corresponding to amino acids 128–152 mapping within a highly conserved domain of human c-fos p62. Human c-fos p62 is a 64 kDa nuclear phosphoprotein induced by a variety of biologically active agents and is a component of the transcriptional regulator, AP-1. (See, e.g., Bohmann et al. (1987), *Science* 238:1386–1392). The antibody c-fos (K-25) reacts with vertebrate c-fos and the well-known functional homologues of c-fos known as fos B, fra-1 and fra-2 by immunoprecipitation, Western blotting and cell staining. See, e.g., Cohen et al. (1989), *Genes and Dev.* 3:173–184 and Nishina et al. (1990), *Proc. Natl. Acad. Sci. USA* 87:3619–3623.

A currently preferred substance for binding to the A/T rich sequence at the 5' end of the OP-1 responsive transcription activating element disclosed herein comprises a polypeptide having an amino acid sequence defining a protein which is capable of binding to the MEF-2 consensus sequence (SEQ. ID No. 6), but which is distinct from MEF -2 protein. (See Example 5 below.) The currently preferred substance is a member of the MEF-2 family, originally termed RSRF for related to serum-responsive factor (SRF) belong to MADS box transcription factors (Olson et al., 1995). MADS box proteins, which include SRF, MCM, Agamous and Defeciens, recognize specific A/T rich response elements as homo or heterodimers and regulate programs of cell type specific gene expression in different organisms. Transcripts of most MEF-2 family members are expressed in a wide range of tissues and established cell lines, however, MEF-2 protein and DNA binding activity are largely restricted to muscle cells and neurons, suggesting cell type specific translation regulation of MEF-2 (Suzuki et al. (1095) *Mol. Cell. Biol.* 15:3415–3423; Olson et al. 1995). As exemplified herein, DNA binding of this MEF-2 protein family member is inducible by a morphogen such as OP-1 and enhanced DNA binding is detectable in a morphogen-responsive cell as early as 2 hrs. following exposure to the morphogen. As is further exemplified herein, the presence of this inducible DNA-binding protein is an indicia of tissue morphogenesis and/or cell differentiation, particularly chondroblast or osteoblast differentiation. Thus, this inducible MEF-2 protein family member can be used to monitor chondrocytic phenotype development, for example, as well as to identify tissues and/or cells competent to respond to morphogen treatment. The instant invention contemplates that this inducible DNA-binding can indicate morphogen-mediated alterations in gene expression at either transcriptional or translational levels; morphogen-mediated alterations in DNA affinity; and/or combinations of the foregoing.

Also contemplated herein are amino acid variants of the present intracellular expression activators, including allelic and species variants thereof or other naturally-occurring or synthetic amino acid sequence variants. As used herein, an "amino acid sequence variant" comprises a polypeptide having an amino acid sequence which differs from the naturally-occurring sequence, yet which retains substantially the same functional properties as the wild type activator reported in the examples below, including at least the binding capacity for nucleotides 682–761 of SEQ. ID No. 1.

It is anticipated that transcriptional activation via the A/T rich sequence or AP-1 like sequence may require a number of DNA-protein, protein—protein or nucleic acid/nucleic acid interactions. It is further anticipated that the region flanking the A/T rich and AP-1 like regions, both within and outside of the transcription activating element may be required for transcriptional activation in some circumstances, e.g. in tissue specific gene expression. Yet further, the relative spacial orientation of the A/T rich and AP-1 like sequences, e.g. the distance between the 3' end of the A/T rich sequence and the 5' end of the AP-1 like sequence, or the distance between the 3' end of the transcription activating element and the transcription start site is critical for transcription activation.

It is contemplated that the substantially pure expression activators can be prepared using well-known purification techniques such as, but not limited to, gel filtration chromatography, affinity chromatography, and high-pressure liquid chromatography. In particular, it can be prepared by ligand-affinity chromatography based upon its binding and/or interaction with the transcription activating element of SEQ. ID No. 1 herein. The skilled artisan need only use routine experimentation to obtain a substantially pure activator in accordance with the instant invention. (See Examples 6 and 7 below).

Accordingly, the present invention further contemplates an isolated polypeptide chain comprising: a morphogen-inducible DNA binding protein which can interact with nucleotides 699–711, 715–724, 699–731, 682–731, 703–724, 682–761 of Seq. ID No. 1; species or allelic variants of the foregoing; truncated amino acid sequences of any of the foregoing inducible by a morphogen or analog thereof under native conditions; and biosynthetic or recombinant variants of all the foregoing.

In a related aspect, the instant invention further provides a method for assessing whether a sample comprises an expression activator. This method involves providing the above-described core DNA sequence or any one of the DNA sequences described herein; contacting the DNA with the sample; and, detecting binding thereto by one or more activators. If desired, an equivalent of the core DNA sequence can be used, including allelic, species and degenerate sequences. "Degenerate sequences" include nucleotide sequences which differ from the present core sequence but which do not alter the binding interaction between the above-described intracellular expression activators and the intact OP-1 responsive transcription activating element. This method provides both an alternative to, or an additional screening assay for, an OP-1 or morphogen analog because, as exemplified below, a morphogen such as OP-1 induces and/or mediates the binding of these substances to the responsive element. Thus, screening for an OP-1 induced interaction, for example, between the DNA and such a substance or substances further characterizes a compound's ability to mimic OP-1, for example. Additionally, the DNAs described herein can be used to probe tissues for the potential to be morphogen-responsive. As exemplified herein, tissue and cell specificity are mediated by binding of certain expression activators to distinct regions of the OP-1 responsive transcription activating element. Exemplary conditions under which such a DNA-protein interaction can be detected have been previously described in Augereau et al. (1986), *EMBO J.* 5:1791–1797, the disclosure of which is herein incorporated by reference. Briefly, protein-containing nuclear extracts are pre-incubated on ice for 15 minutes with *E. coli* DNA in 10% glycerol, 10 mM Hepes, pH 7.9, 50 mM KCl, 5 mM $MgCl_2$, 0.5 mM DTT; upon addition of the particular DNA sequence of interest, incubation is allowed to continue for 15 minutes to permit protein-DNA complex formation.

In yet another aspect, the invention provides a cell for the inducible expression of a morphogen. This cell has a first DNA encoding a morphogen; a second DNA in transcriptionally operative association with the first DNA, the second DNA comprising one embodiment of the above-described OP-1 responsive transcription activating elements, or a functional equivalent thereof. The cell further comprises cellular means for producing one or more intracellular substances (expression activators) that bind with one or more portions of the second DNA so as to stimulate expression of the morphogen encoded by the first DNA when the cell is contacted with an extracellular inducing agent. In certain preferred embodiments, the extracellular inducing agent is a morphogen or an analog thereof identified according to the inventive principles set forth herein. In certain embodiments, the extracellular inducing agent is OP-1 or an analog thereof.

The foregoing cell is a mammalian cell, preferably a primate cell, most preferably a human cell. In certain embodiments, the foregoing cell is a murine cell such as a mouse, rat or hamster cell. The cell of the instant invention can be naturally-occurring, immortalized in culture or constructed by recombinant or cell fusion technologies.

It will be appreciated that the present invention can be used to construct a cell for the inducible expression of any desired gene product and is not limited to use with first DNA encoding a morphogen. In still another aspect, the invention provides methods for inducing expression, including autocrine expression, of a morphogen, e.g., OP-1, indeed of a gene product using the above-described cells. In these methods, one of the above-described cells is contacted with OP-1, a morphogen or a morphogen analog under conditions sufficient to induce expression of the gene product encoded by the first DNA.

Optionally, the foregoing methods can be carried out in vivo by providing any one of the above-described cells to a mammal. In these embodiments, the contacting step is carried out by administering an inducing agent to the mammal. This method is particularly well suited for administering a morphogen such as, but not limited to, OP-1 to a mammal afflicted with a metabolic bone disease or other injury, disease or condition for which long-term administration of the morphogen is anticipated to provide a clinical benefit.

In yet another currently preferred embodiment, the invention provides DNA for inducing a morphogen mediated biological effect. This DNA defines a morphogen-responsive transcription activating element and a cloning site suitable for insertion of a reporter gene encoding a detectable gene product, or a therapeutic gene encoding a biologically active gene product. When the reporter gene is inserted at the cloning site, the reporter gene is operatively associated with the morphogen-responsive transcription activating element such that the detectable gene product is produced when the DNA is present in a morphogen-responsive cell and the cell is contacted with a morphogen or an analog thereof. In certain currently preferred embodiments, the morphogen-responsive transcription activating element is responsive to OP-1 or an analog thereof. The materials and protocols for inserting reporter genes within pre-existing cloning sites are readily available and well-known in the art. See, for example, *Molecular Cloning: A Laboratory Manual* (eds., Maniatis et al.; Cold Spring Harbor Press, Cold Spring Harbor; 2nd edition)(1989). The skilled artisan need only exercise routine experimentation to prepare DNAs of the present invention.

The present invention provides a method and cells with which candidate morphogens or morphogen analogs can be evaluated for their ability to mimic morphogens or to inhibit morphogens (e.g., morphogen agonists or antagonists) by monitoring the effect of the analogs on an appropriate morphogen responsive cell line. Morphogen agonists are anticipated to have utility in any application where tissue morphogenesis is desired, such as in the regeneration of damaged tissue resulting from mechanical or chemical trauma, degenerative diseases, tissue destruction resulting from chronic inflammation, cirrhosis, inflammatory diseases, cancer and the like, and in the regeneration of tissues, organs and limbs. Morphogen antagonists are envisioned to have utility in applications where tissue morphogenesis is to be limited as, for example, in the treatment of malignant transformations, including, but not limited to, osteosarcomas, Paget's disease, and fibrodysplasia ossificans progressive (See, for example, Roush (1996), *Science* 273:1170).

Accordingly, for ease of practice of the invention set forth herein, a kit is provided for screening candidate substances for morphogen mimetic properties as is a kit for preparing a cell for the inducible production of a gene product. The kits herein comprise a receptacle for containing DNA, and DNA defining an OP-1 responsive transcription activating element and a cloning site suitable for insertion of a gene in operative association with the activating element. Optionally, the DNA comprises a reporter gene encoding a detectable gene product, e.g., a product having detectable enzymatic activity. In certain embodiments, kits further contain means for inducing a cell to internalize the present DNA. Certain other kits contain a morphogen and/or a compound identified by the methods of the instant invention as having the ability to induce a morphogen-mediated or OP-1 mediated biological effect. These optional kit components are useful as control substances for practice of the identification methods disclosed herein.

Practice of the invention will be still more fully understood from the following examples, which are presented herein for illustration only and should not be construed as limiting the invention in any way.

EXAMPLE 1

Effect of OP-1 on the Proliferation and Differentiation of C5.18 Cells

To characterize the biological effects of OP-1 on bone derived cell lines, OP-1 responsiveness was examined in C5.18 cells, spontaneously immortalized fetal rat calvaria cells well-known in the art and described, for example, in Grigoriadis et al. (1990) *Developmental Biology* 142:313–318 and in Von Schroeder et al. (1994) *Teratology* 50:54–62, the disclosures of which are herein incorporated by reference. C5.18 cells were plated in 12-well culture dishes ($1 \times 10^5$ cell/well) in αMEM containing 15% fetal bovine serum. As described below, varying amounts of recombinant human OP-1 (Creative BioMolecules, Inc., Hopkinton, Mass.) were added to the culture media and the calvaria cells were incubated with the OP-1 containing medium for varying lengths of time as indicated below. OP-1 was prepared and formulated generally as earlier described in U.S. Pat. Nos. 5,258,494; 5,266,683; and 5,354,557, the disclosures of which are incorporated herein by reference.

Briefly, OP-1 treatment of fetal rat calvaria cells induced mitogenesis and phenotypic markers for chondrocytes and osteoblasts. For example, OP-1 induced type II collagen, a marker for chondrocytes, and type X collagen, a specific marker for hypertrophic chondrocytes, respectively. Subsequently, OP-1 induced type I collagen and the osteoblastic markers, osteocalcin and alkaline phosphatase. The order of appearance of these molecular markers recapitulated the sequence of events observed during endochondral bone morphogenesis as induced in vivo by OP-1. See U.S. Pat. No. 4,968,590 and Sampath et al. (1983) *Proc. Natl. Acad. Sci. USA* 80:6591–6595, the disclosures of which are incorporated herein by reference.

The osteoblastic markers alkaline phosphatase and osteocalcin, as well as the chondrocytic markers types II and X collagen, were examined using standard techniques for RNA blot analysis such as those disclosed in Harada et al. (1994) *J. Clinical Investigation* 93:2490–2496. cDNA probes for rat alkaline phosphatase and osteocalcin were prepared in accordance with art-recognized methods such as, for example, those disclosed in Yoon et al. (1987) *Biochem. Biophys. Res. Commun.* 148:1129–1136. cDNA probes for mouse types II and X pro-collagen were also prepared in accordance with art-recognized methods such as those disclosed in Asahina et al. (1993) *J. Cell Biology* 123:921–933 and Chen et al. (1995) *J. Cell Science* 108:105–114, respectively. Relevant teachings of each of the aforementioned references are incorporated herein by reference.

Specifically, 300 ng/ml OP-1 induced mitogenesis (FIG. 1) as measured by $^3$H-thymidine incorporation studies practiced generally according to art-recognized methods. FIG. 1 illustrates that OP-1 (300 ng/ml) stimulated $^3$H-thymidine uptake. This same result was not obtained in control cultures without OP-1 or cultures treated only with TGFβ (porcine; Catalog #102-B2, R and D Systems, Inc., Minneapolis, Minn.).

Figure 2:
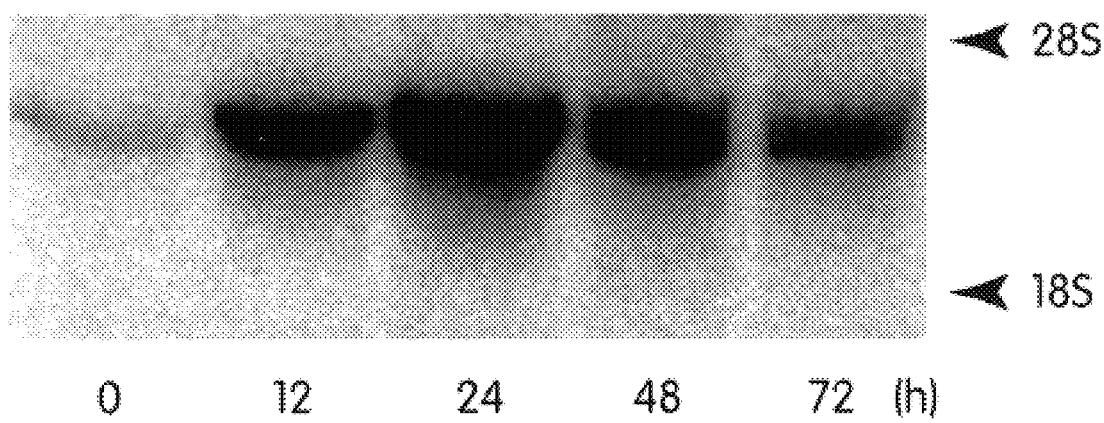
FIG. 2 is an autoradiograph of results of an RNA blot analysis demonstrating the effects of OP-1 on type X collagen mRNA levels in C5.18 fetal calvaria cells over a 72 hour period.
Figure 3:
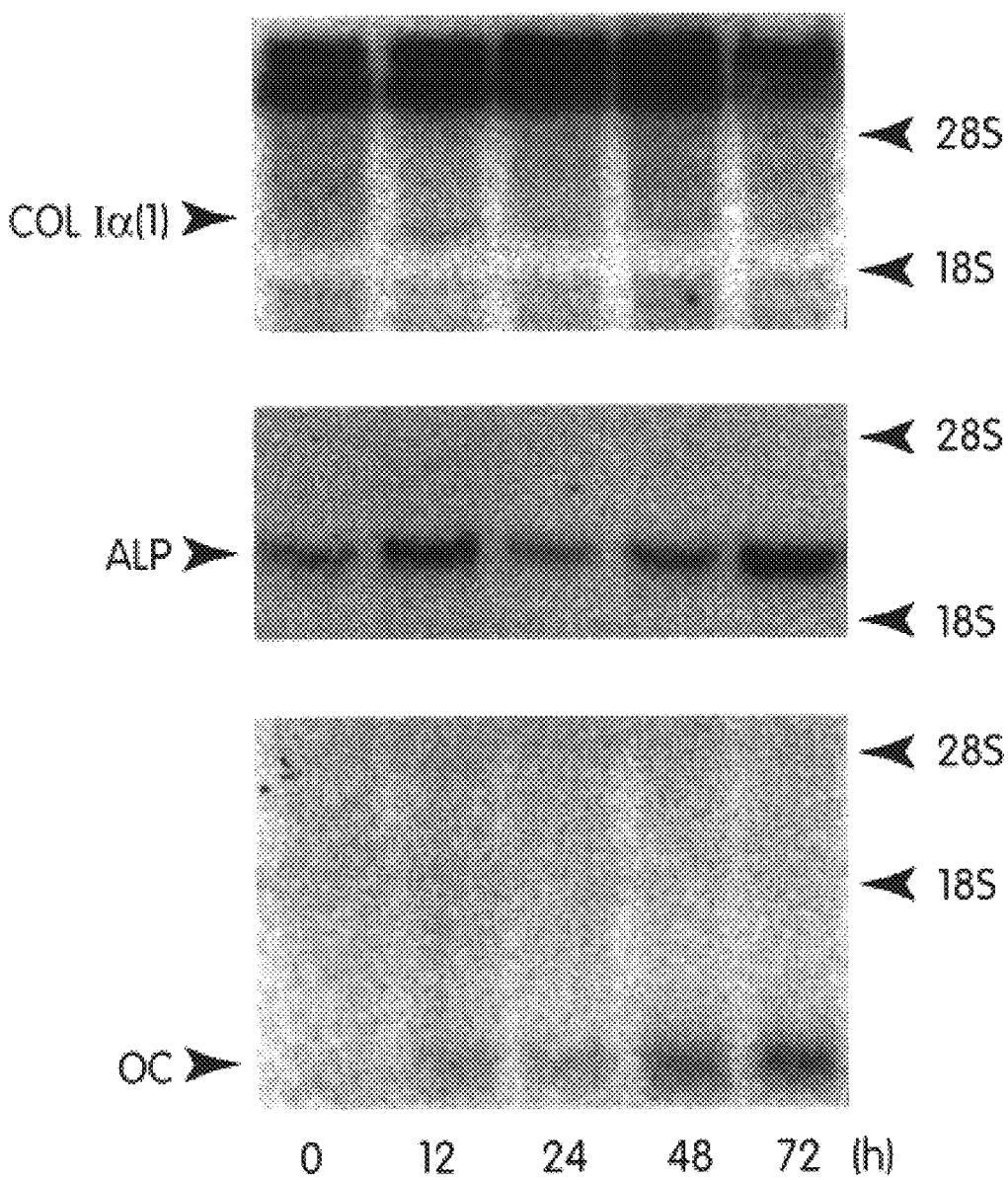
FIG. 3 is an autoradiograph of results of an RNA blot analysis demonstrating the effects of OP-1 on the mRNA levels of osteoblastic phenotypic markers type I collagen, alkaline phosphatase and osteocalcin in C5.18 cells over a 72 hour period.

The effects of OP-1 on expression of phenotypic markers for chondrocytes and osteoblasts were also studied. As illustrated in C5.18 cells, OP-1 induced type II collagen, a marker for matrix-producing chondrocytes, and type X collagen, a specific marker for hypertrophic chondrocytes, to peak levels by 12 h and 24 h, respectively (FIG. 2). Further, OP-1 induced type I collagen at 48 h and, at 72 h, induced expression of osteocalcin and alkaline phosphatase, both of which are well-characterized as osteoblastic markers (FIG. 3). Still further, OP-1 also induced mRNA for N-cadherin, N-CAM and MSX-2, further suggesting that OP-1 causes differentiation of C5.18 cells into chondrocytes and/or osteoblasts. Yet further, mRNA for ALK3 and ALK6, specific type 1 receptors for BMPs, were highly expressed in C518 cells, suggesting that OP-1 acts on specific BMP receptors to induce chondrocyte differentiation.

Figure 4:
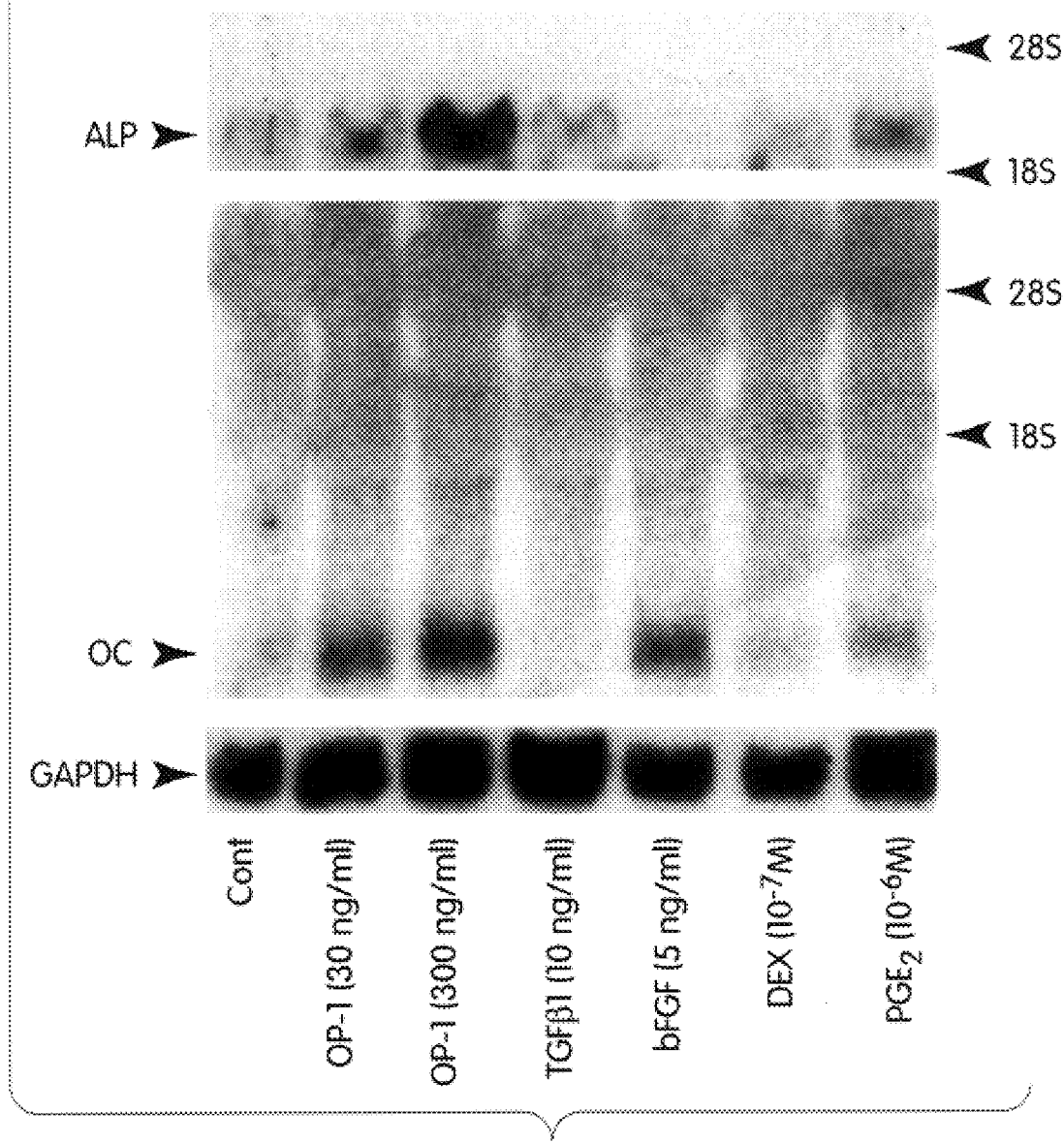
FIG. 4 is an autoradiograph of results of an RNA blot analysis demonstrating the effects of OP-1 and TGFβ on osteoblastic phenotypic markers alkaline phosphatase and osteocalcin in C5.18 cells.
Figure 5:
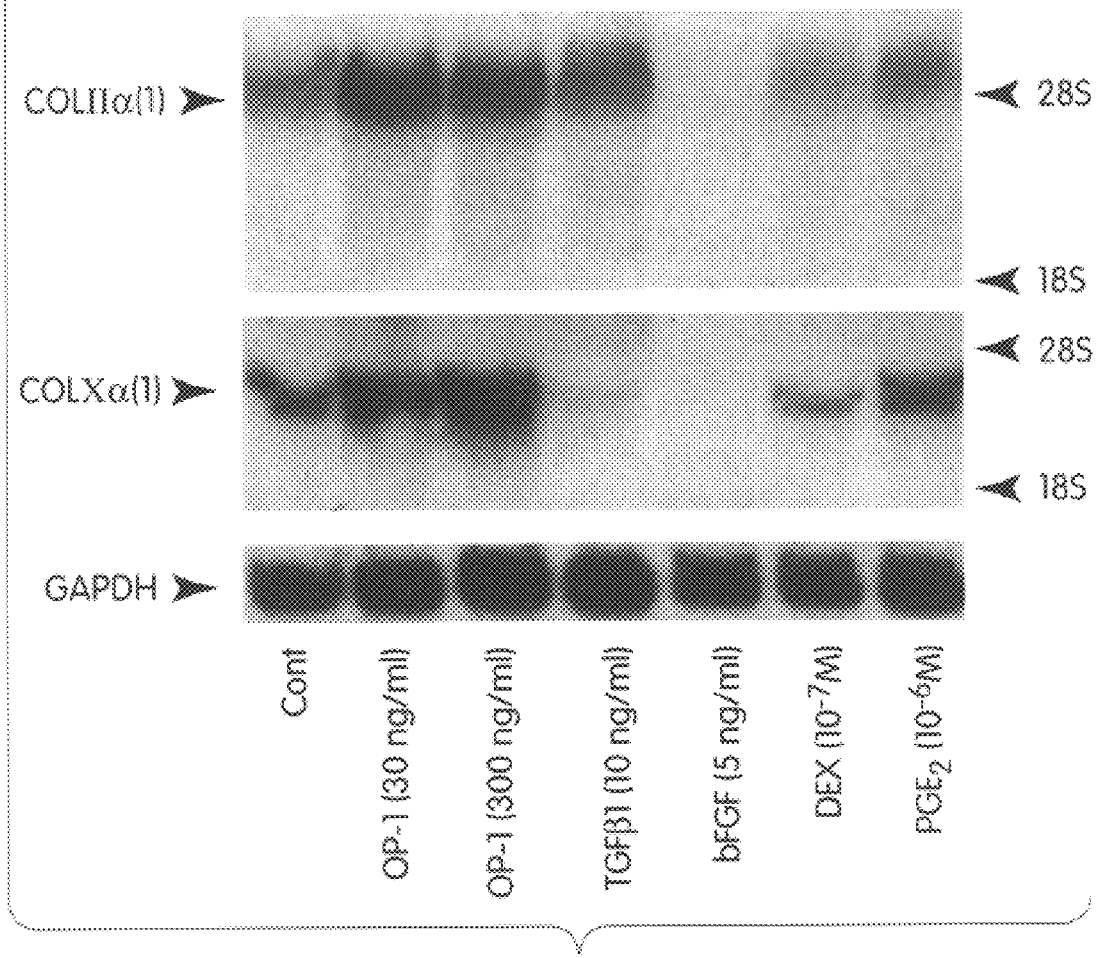
FIG. 5 is an autoradiograph of results of an RNA blot analysis demonstrating the effects of OP-1 and TGFβ on mRNA levels of chondrocytic phenotype markers types II and X collagen in C5.18 cells.

Thus, in fetal rat calvaria cells, OP-1 induced a cascade of molecular events resembling the sequence of events induced in vivo by OP-1 and culminating in endochondral bone formation. OP-1 also induced formation of nodules positive for alkaline phosphatase (FIG. 4). In contrast, TGFβ elicited a negligible effect on the expression of these same osteoblastic (FIG. 4) or chondrocytic markers (FIG. 5) and did not increase collagen X mRNA levels in C5.18 cells. These observations suggest that C5.18 cells provide a useful cell culture model for assessing whether test substances function as OP-1 analogs, as well as for further delineating one or more of the biological mechanisms associated with OP-1 induced chondrocyte and/or osteoblast differentiation.

Those of skill in the art will appreciate that the general principles and parameters of the C5.18-based in vitro model system, including monitoring expression of phenotypic markers such as types I, II and X collagen, and alkaline phosphatase, can be adapted easily to other readily available cell culture systems. See, e.g., Manduca et al. (1992) *Cell Biology* 57: 193–201 for a description of a chick embryo osteoblast in vitro assay system; Reginato et al. (1993) *Dev. Dyn.* 198: 284–295 for a description of a chick embryonic sternum system; Asahina et al. (1993) *J. Cell Biology* 123: 921–933 for a description of an in vitro system using primary cultures of newborn rat calvaria. The disclosures of the aforementioned prior art references are incorporated herein by reference.

EXAMPLE 2

Effects of OP-1 on Type X Collagen Promoter Reporter Constructs

The above-described effect of OP-1 on the expression of type X collagen was of particular interest, as this phenotypic marker is generally understood to be specific for hypertrophic chondrocytes and thus of endochondral bone formation. The mouse type X collagen gene promoter was therefore employed as a model in order to examine the molecular mechanisms for OP-1 induction of chondrocyte phenotypic markers. The responsiveness of the type mouse X collagen gene promoter to OP-1 was therefore studied using the below described luciferase reporter gene deletion analyses:

The promoter region of the mouse type X collagen gene (nucleotides 1 to 1067, as designated by Elima et al. (1993) *Biochem. J.* 289:247–253, and by GenBank EMBL Data Bank: Accession #X67348; COLl0A1 gene; collagen alpha 1 type X)(also designated herein as nucleotides 1–1067 of SEQ. ID No. 1) was cloned according to well-known PCR (polymerase chain reaction) methods from mouse genomic DNA (Clonetech, Palo Alto, Calif.) using a 34 base pair 5' primer carrying the KpnI site and a 33 base pair 3' primer carrying the MluI site. These primer sequences were confirmed using the sequence of the mouse type X collagen promoter as published in Elima et al. (1993) *Biochem. J.* 289:247–253, the disclosure of which is incorporated herein by reference. The sequence of cloned type X collagen promoter DNA used herein was confirmed by nucleotide sequencing, using the Sequence Version 2.0 DNA Sequencing Kit available from USB (United States Biochemical, Cleveland, Ohio).

Figure 6:
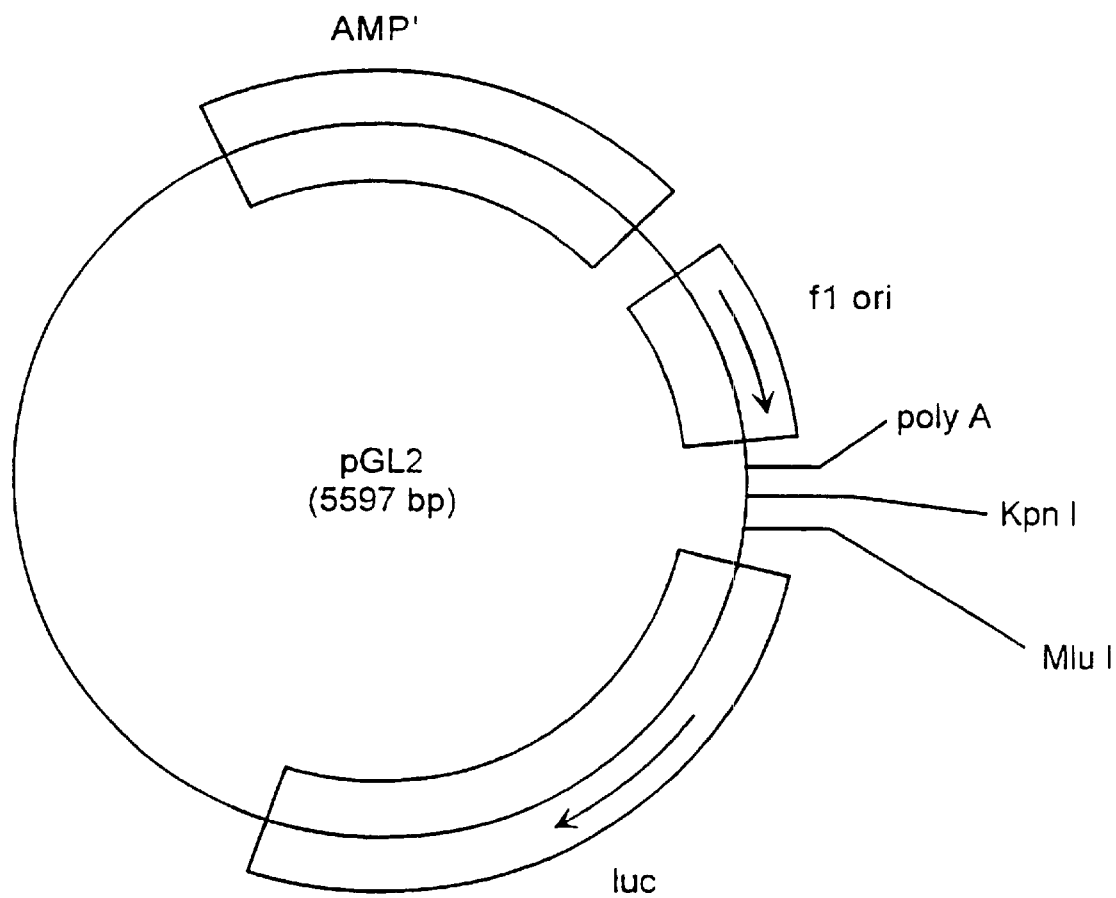
FIG. 6 is a vector map depicting an exemplary vector with a promoterless luciferase reporter gene and the KpnI and MluI restriction enzyme cloning sites.

The cloned promoter DNA was used to prepare a series of deletion construct vectors carrying the luciferase reporter gene and portions of the mouse type X collagen gene. A promoterless pGL2-basic plasmid comprising a nucleotide sequence encoding the detectable enzyme luciferase (Promega, Madison, Wis.) was employed as the basic vector (FIG. 6). Transfection efficiencies were monitored with parallel transfections using a pGL2—Promoter Vector (Promega) and the results were standardized by calculating relative promoter activity. The above-described intact mouse type X collagen promoter sequence (nucleotides 1–1067, SEQ. ID No. 1) was inserted into the pGL2 plasmid following digestion with KpnI and MluI. Serial 5' deletion fragments (renumerated in FIG. 7) were similarly prepared by PCR methods as described above and subcloned into KpnI and MluI digested preparations of the pGL2 plasmid. Thus, the cloned promoter DNA or a portion thereof was placed in transcriptionally operative association with the luciferase reporter gene.

The foregoing vectors were transfected into rat C5.18 calvaria, NIH3T3, C2C12 and ROS17/2.8 cells, using standard art known techniques such as calcium phosphate precipitation, electroporation in Gene Pulser Cuvettes (BioRad Labs., Melville, N.Y.) using a Gene Pulser (BioRad Labs) at 960/$\mu$FD/250V, or a diethylamino ethyl—dextran method. Briefly, for example, cells were plated in 12-well culture dishes ($1 \times 10^5$ cell/well) in $\alpha$MEM containing 15% fetal bovine serum (complete media). Forty-eight to seventy-two hours later, cells were harvested and incubated for 6 h with 2 $\mu$g/ml of the above described deletion constructs and which were previously precipitated at 20 $\mu$g/ml in 25 mM Hepes (pH 7.1)/140 mM NaCl/0.75 mM $Na_2HPO_4$/0.124M$CaCl_2$. A 10% solution DMSO in PBS was used to terminate transfection. Thereafter, transfected cells were cultured in complete media. Twenty-four hours later, transfected cells were contacted with 100 ng/ml recombinant human OP-1, 2 ng/ml porcine TGF$\beta$ (R&D Systems, Minneapolis, Minn.) or 10 ng/ml basic fibroblast growth factor (bFGF, R&D Systems) and further cultured for an additional 24 hours. Luciferase activity induced by the exogenously added OP-1, TGF$\beta$ or bFGF was measured using the Promega Luciferase Assay System (Promega, Madison, Wis.).

Figure 7:
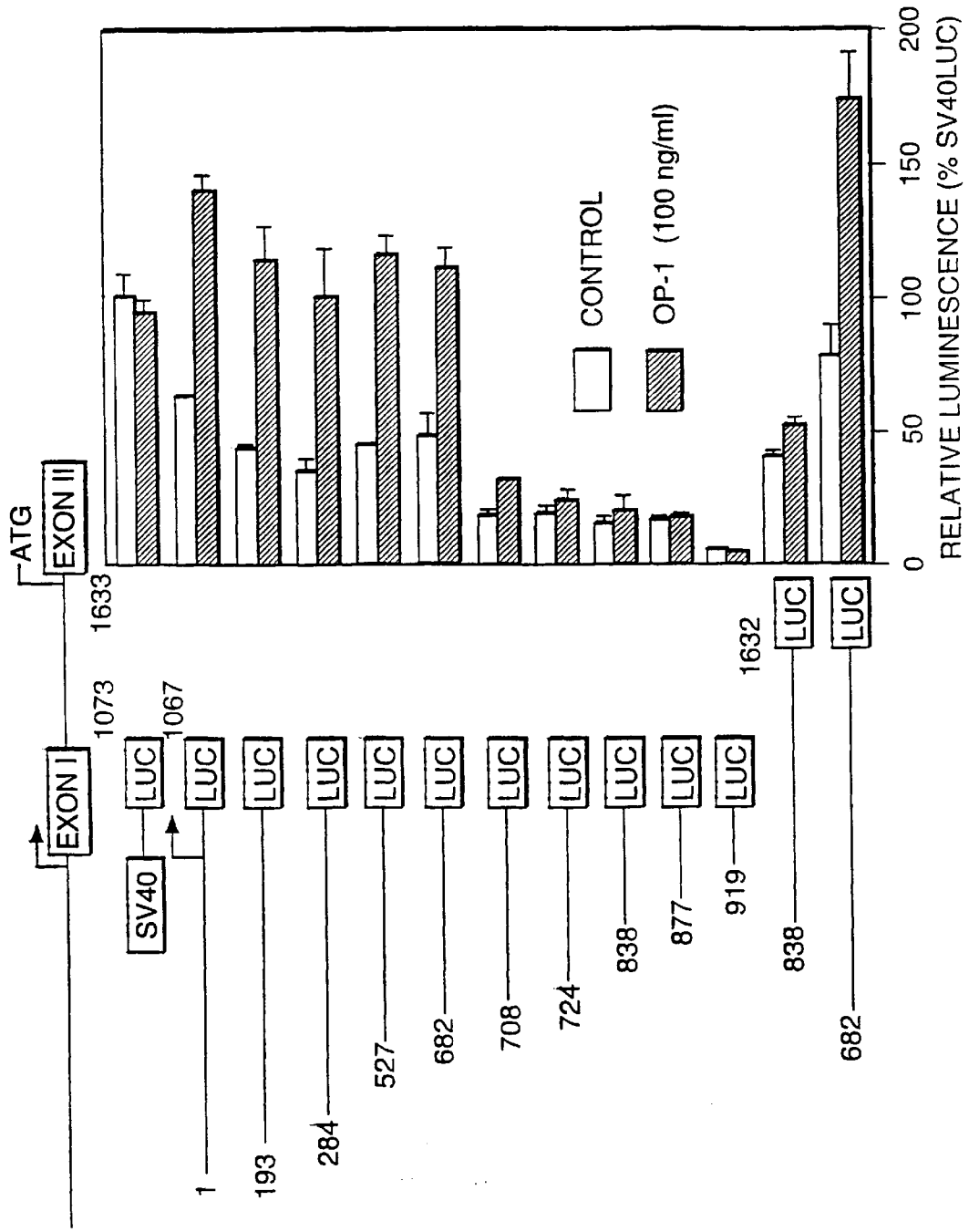
FIG. 7 is a bar graph depicting OP-1 induced luminescence produced by C5.18 fetal calvaria transfected with various deletion constructs of the mouse type X collagen promoter operatively associated with the luciferase reporter gene and transfected into C5.18 fetal calvaria and subsequently contacted with OP-1.

As illustrated in FIG. 7, OP-1 treatment (100 ng/ml) stimulated the luciferase activity of the intact type X collagen construct containing the 1–1067 (SEQ. ID No. 1) base pair fragment of the collagen type X promoter (1–1067COLXLUC). This same amount of OP-1 stimulated the construct containing a 386 base pair fragment (682–1067 of SEQ. ID No. 1) of the COLX promoter up to 3 fold in a dose dependent manner. However, deletion of a further 42 base pair 5' fragment abolished OP-1 responsiveness. This result suggested that at least the nucleotides at positions 682–724 of SEQ. ID No. 1 are required for OP-1 responsiveness of the type X collagen gene.

The stimulatory effects of OP-1 on the collagen X promoter were not observed in ROS 17/2.8 osteoblastic cells, in NIH3T3 fibroblastic cells, or in C2C12 myoblasts (Table I), suggesting that OP-1 exerts its effects in a tissue specific manner.

TABLE I*

| | 1-1067COLXLUC | | SV40LUC OP-1 | |
|---|---|---|---|---|
| Cell Line | Control | OP-1(100 ng/ml) | Control | (100 ng/ml) |
| C5.18 | 62.7 ± 1.7 | 139.9 ± 9.3 | 100 | 94.5 ± 8.5 |
| ROS17/2.8 | 52.1 ± 12.6 | 70.2 ± 7.1 | 100 | 106.7 ± 19.9 |
| NIH3T3 | 122.2 ± 7.3 | 105.9 ± 19.0 | 100 | 103.3 ± 17.5 |
| C2C12 | 104.9 ± 7.4 | 123.9 ± 2.1 | 100 | 92.2 ± 8.5 |

*The data are presented as the relative mean luciferase activity (% SV40) LUC) ± SD.

Figure 8:
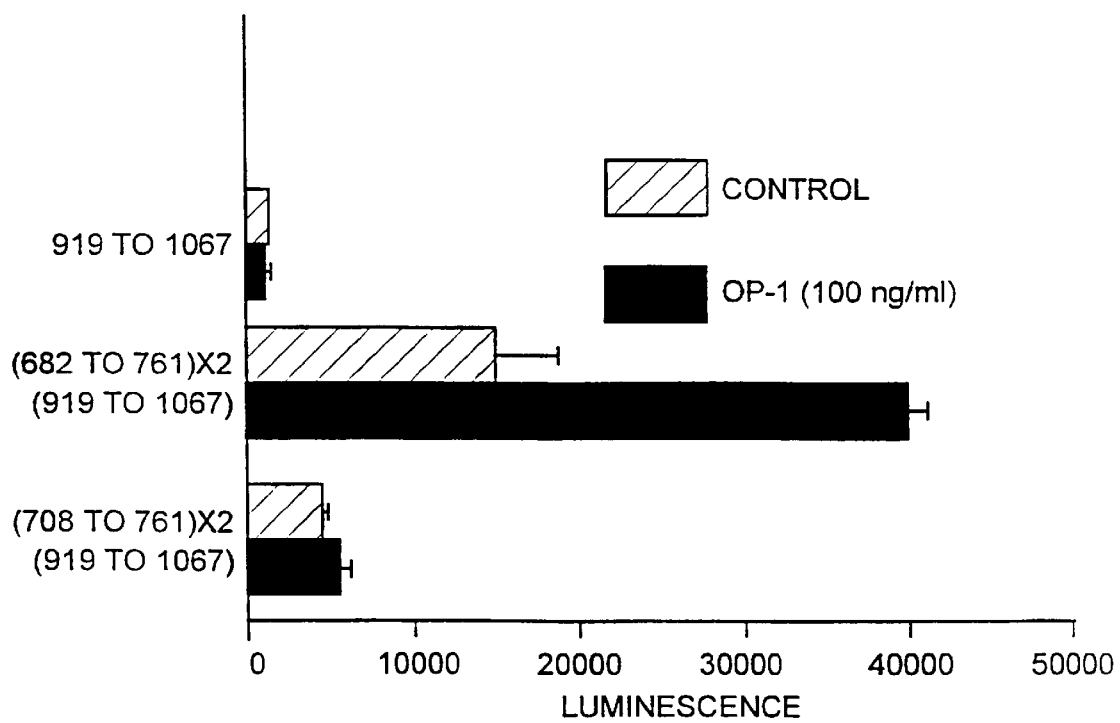
FIG. 8 is a bar graph depicting OP-1 induced luminescence produced by C5.18 fetal calvaria transfected with selected deletion constructs which confer OP-1 responsiveness to a minimum segment of the homologous mouse type X collagen promoter.
Figure 9:
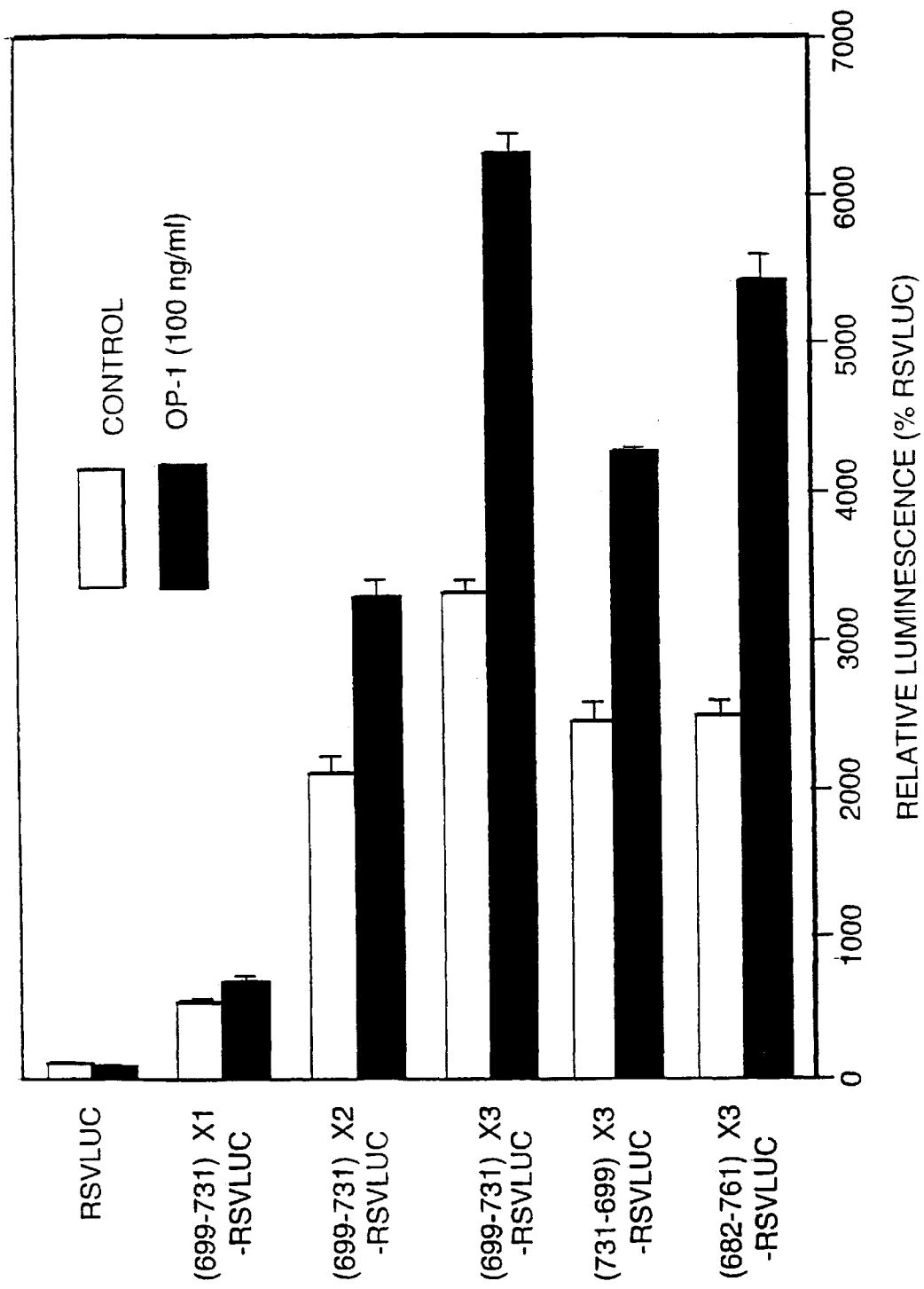
FIG. 9 is a bar graph depicting OP-1 induced luminescence produced by C5.18 fetal calvaria transfected with selected deletion constructs which confer OP-1 responsiveness to a minimum segment of the heterologous RSV promoter.
Figure 10:
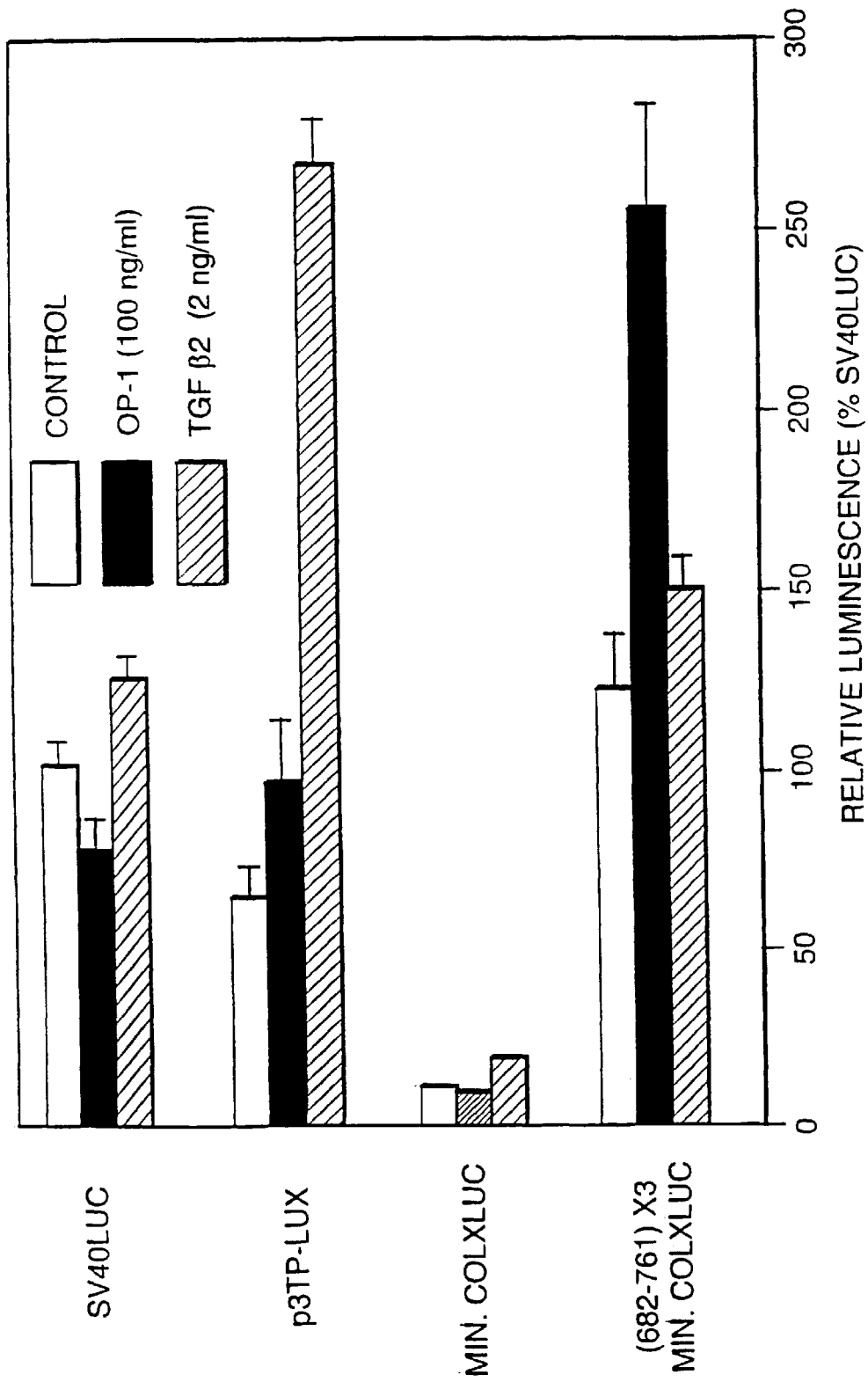
FIG. 10 is a bar graph depicting the effects of OP-1 and TGFβ on induction of a reporter gene operatively associated with the mouse type X collagen minimum promoter, as compared to induction of SV40LUC and p3TP-LUX vectors.

Further studies confirmed that the 80 nucleotide fragment comprising residues 682–761 of SEQ. ID No. 1 is sufficient to confer OP-1 responsiveness to the mouse collagen type X "minimum" promoter or to the heterologous Rous Sarcoma Virus (RSV) "minimum" promoter in C5.18 cells. Portions of the collagen type X promoter were placed in operative association with the collagen "minimum" promoter (minCOLXLUC) (nucleotides 919–1067 of SEQ. ID No. 1), according to the methods described herein above, and the RSV "minimum" promoter" (RSVLUC) (see, for example, Towler et al. (1995) *Endocrinology* 136:1089–1096, the disclosure of which is incorporated herein by reference). Both "minimum" promoters, when transfected into mammalian cells, do not confer responsiveness to OP-1. For the RSV constructs, synthetic double stranded oligonucleotides corresponding to nucleotides 699–731 of SEQ. ID No. 1 of the mouse collagen type X promoter were ligated into the BglII site of RSVLUC, creating (699–731)x1RSVLUC (containing one copy of nucleotides 699–731 of SEQ. ID No. 1), (699– 731)x2RSVLUC (containing two copies of nucleotides 699–731 of SEQ. ID No. 1), (699–731) x3RSVLUC (containing three copies of nucleotides 699–731 of SEQ. ID No. 1), and (731–699)x3RSVLUC (containing three copies of nucleotides 699–731 of SEQ. ID No. 1 in reverse orientation). Three copies of the (nucleotides 682–761 SEQ. ID No. 1) fragment were also inserted into the RSVLUC vector, creating (682–761) x3RSVLUC. The (682–761 of SEQ. ID No. 1) collagen X promoter region conferred OP-1 responsiveness to both the mouse collagen type X minimum promoter (FIG. 8) and the RSV minimum promoter (FIG. 9) in C5.18 cells. A further 26 nucleotide deletion (leaving nucleotides 708–761 of SEQ. ID No. 1) abolished the OP-1 response in the collagen type X minimum promoter (FIG. 8). Consistent with these results, a construct containing the 699–731 region of SEQ. ID. NO. 1 in operative association with the RSV minimum promoter conferred OP-1 responsiveness in a copy number dependent and orientation independent manner, to a similar extent as the 682–761 of SEQ. ID No. 1 fragment (FIG. 9). In contrast, TGF$\beta$2 (2 ng/ml) had little effect on the OP-1 responsive element (nucleotides 682–761 of SEQ. ID No. 1) in the minimum RSV promoter construct (FIG. 10), despite confirmation that the same TGF$\beta$ preparation successfully induced a 4 fold stimulation of a p3TP-Lux vector construct borne by C5.18 cells transfected according to the procedure described above. OP-1 was less effective than TGF$\beta$ in stimulating the p3TPLux construct, suggesting that OP-1 specifically upregulates the collagen type X promoter and its mRNA levels and that OP-1 and TGF$\beta$ may stimulate gene expression via distinct mechanisms in C5.18 cells.

In addition, a number of reporter vectors were constructed and tested which confirmed the above results for the responsiveness of the mouse collagen type X promoter to OP-1 in C5.18 cells. OP-1 stimulated the reporter activity of a promoter construct including the first intron of the mouse collagen type X gene, which was abolished by a 5' 42 nucleotide deletion (682–724 of SEQ. ID No. 1) (FIG. 7). OP-1 also upregulated the luciferase reporter activity driven by the nucleotides 1–913 of the collagen X promoter region, which contains only the upstream transcription start site and is 20 fold less active than 1–1067 containing both transcription start sites.

Further studies resting on 3' deletion analysis of the RSV promoter construct more precisely identified the OP-1 responsive element as a 50 base pair sequence spanning positions 682–731 of SEQ. ID No. 1. Furthermore, deletion of 26 base pairs (removing nucleotides 682–707 of SEQ. ID No. 1) abolished OP-1 responsiveness. Consistent with these results, OP-1 had no effect on the luciferase activity driven by three copies of the consensus AP-1 sequence B (GTGACTCAGCGCGGA) (SEQ. ID No. 5) fused to the human fibrinogen "minimum" promoter, which was upregulated by bFGF, suggesting that the 5' A/T rich sequence spanning nucleotides 699–711 of SEQ. ID No. 1 is required for OP-1 responsiveness.

The foregoing studies culminated in the discovery and characterization of an OP-1 responsive element in the mouse collagen type X gene promoter. As is exemplified below in Example 4, a core region (33 nucleotides) of this OP-1 responsive element is bound by one or more substances present in nuclear extracts produced from OP-1 stimulated C5.18 cells.

EXAMPLE 3

Mutation Analysis of the Transcription Activating Element

Figure 12:
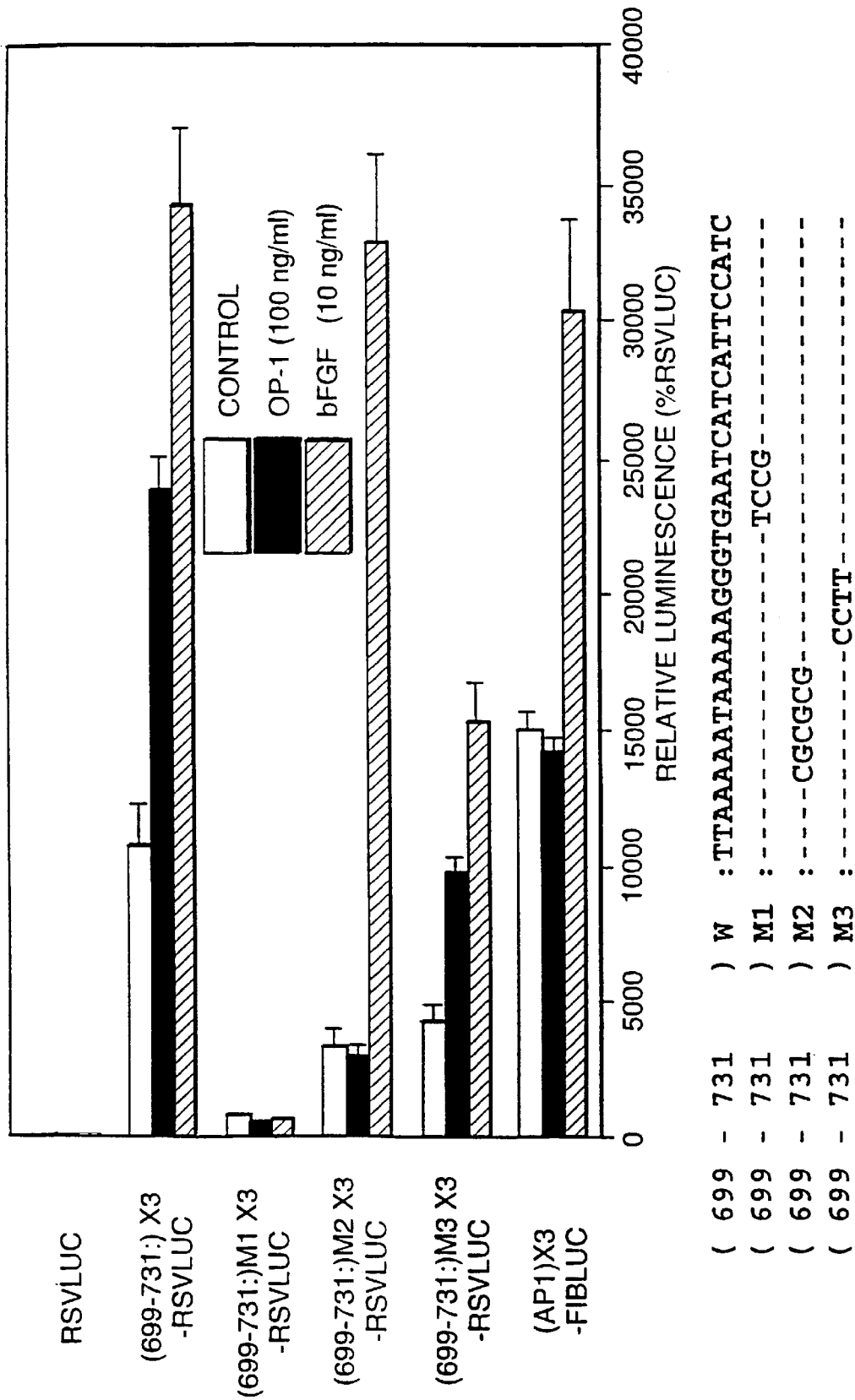
FIG. 12 is a bar graph depicting mutation analysis of the (nucleotides 699–731 of Seq. ID No. 1) mouse collagen type X promoter region. The mutant sequences are diagrammed below the bar graph.

To characterize the respective roles of the AP-1 like (nucleotides 715–724 of SEQ. ID No. 1) and the A/T rich sequences (nucleotides 699–711 of SEQ. ID No. 1) (both of which are depicted within sequence "w" in FIG. 12) in the OP-1 driven induction of the collagen X promoter, mutations of the nucleotides 699–731 (SEQ. ID No. 1) upstream of the heterologous RSV promoter were analyzed (FIG. 12). Mutation of a portion of the AP-1 like sequence (nucleotides 715–724 of SEQ. ID No. 3) which changes the sequence (GAAT) to (TCCG) (depicted as sequence "M1" in FIG. 12) strongly suppressed the enhancer activity of this region and abolished the stimulatory effects of OP-1 (100 ng/ml) on this region. The above mutation also abolished the stimulatory effects of bFGF (10 ng/ml), which is capable of inducing the expression of the (699–731)x3-RSV construct in the presence of 1% serum (FIG. 12). In contrast, mutation of a portion of the A/T rich sequence (nucleotides 699–711 of SEQ. ID No. 1) which changes the sequence (TAA AAATAA) to (TAACGCGCG) (depicted as sequence "M2" in FIG. 12), abolished the OP-1 induction, but has little effect on the enhancer activity or on the stimulatory effect of bFGF on the site defined by nucleotides 699–731 of SEQ. ID No. 1. Mutation of the AAGGG sequence (nucleotides 710–714 of SEQ. ID No. 1), which adjoins the AP-1 like sequence with the adjacent A/T rich sequence, to (CCTTG), (depicted as sequence "M3" in FIG. 12), suppressed the enhancer activity up to 50% but had no effect on OP-1 or bFGF stimulation. These results suggest that OP-1 acts on the A/T rich site to upregulate the promoter activity, which also requires the AP-1 like site present in this region, while bFGF acts directly on the AP-1 like site to stimulate transcription. This is consistent with the results presented in Example 2 for the AP-1 sequence fused to the human fibrinogen "minimum" promoter which was not induced by OP-1.

EXAMPLE 4

Definition of the Collagen X Transcription Activation Element and Characterization of its Interaction with Nuclear Proteins ("Expression Activators")

The mouse collagen type X promoter was analyzed by DNase footprinting and electrophoretic gel shift assays to further define the OP-1 responsive region and to determine binding specificities and affinity of the expression activators required for the expression of the collagen type X gene. DNase footprinting and gel shift assays were carried out according to techniques well known to those skilled in the art. DNase footprinting was carried out using a nucleic acid probe comprising nucleotides 682–761 of SEQ. ID No. 1. Footprinting analysis showed that a nuclear extract from C5.18 cells protected a 21 nucleotide region, corresponding to nucleotides 703–724 of SEQ. ID No. 1, from degradation by DNase I. The protected region comprised both the 5' A/T rich binding site and the adjacent 3' AP-1-like binding site sequence depicted in SEQ. ID No. 1.

The interaction of the collagen type X promoter with nuclear proteins was further characterized by gel shift assays using the oligonucleotide probes corresponding to the 699–731 of SEQ. ID No. 1, with and without mutations at the AP-1 like sequence and/or at the A/T rich sequence (see FIG. 12). Briefly, cells were lysed and nuclear extracts were prepared and incubated with a radiolabelled oligonucleotide of choice, by methods well known to the skilled artisan. Binding of one or more of the protein components of the extract to the oligonucleotide produces DNA/protein complexes having retarded electrophoretic mobility relative to the mobility of the uncomplexed oligonucleotide DNA probe. These assays demonstrated that exposure of C5.18 cells to OP-1 induced about a 2–3 fold increase in the amount or activity of a nuclear extract component, presumably one or more proteins, that bind to the minimal OP-1 responsive 33 base pair fragment of the mouse collagen type X promoter (nucleotides 699–731 of SEQ. ID No. 1) as demonstrated by increased intensity of the band corresponding to the shifted oligonucleotide. Gel shift assays of nuclear extracts of C5.18 cells incubated with the wild type mouse collagen type X (nucleotides 699–731 of SEQ. ID No. 1) probe showed multiple retarded bands, which were competed with excess cold homologous oligonucleotide, confirming their identity as specific DNA/protein complexes. For example, an oligonucleotide corresponding to the consensus AP-1-like sequence competed for one band, band C, but not bands A or B. In addition, band A but not band B was competed by excess cold collagen type X oligonucleotide (nucleotides 699–731 of SEQ. ID No. 1) with a mutation at the A/T rich sequence (see M2, FIG. 12) which suggested that the mutation abolished specific binding of the oligonucleotide with the protein component of band B (see FIG. 12). These results suggest that band C corresponds to one or more nuclear proteins that interact with the AP-1 like sequence and that band B corresponds to one or more nuclear proteins that interact with the A/T rich sequence. Consistent with these results, using the collagen type X (nucleotides 699–731 of SEQ. ID No. 1) probe with a mutation at the AP-1 like sequence (see M1, FIG. 12), abolished band C but not bands A or B and a probe containing both the mutation in the AP-1 like sequence and the A/T rich sequence abolished band B and not bands A or C.

Supershift assays, in which the nuclear extract-oligonucleotide complexes are further retarded by complexing with specific antibody, were used to determine the identity of the AP-1 binding protein. In these assays, the previously described protein-oligonucleotide probe complexes are further incubated with specific antibody and subjected to electrophoresis, according to art known methods. The OP-1 induced DNA protein complexes from C5.18 and C2C12 cells could be supershifted during gel analysis when treated with an anti human c-fos antibody against the conserved domain of Fos family members (amino acids 128–152 of human c-fos; Catalog #sc-253 from Santa Cruz Biotechnology, Inc., Santa Cruz, Calif.) (SEQ. ID No. 4). This supershift was reversed by the antigenic peptide, suggesting the involvement of Fos family proteins in this complex. However, the OP-1 induced protein-DNA complex did not appear to be super-shifted by antibodies specifically reactive with the related proteins c-fos, fos-B, fra-1, fra-2 or c-jun. UV cross-linking was carried out using the core 33 nucleotide probe sequence (699–731, SEQ. ID. NO. 1) complexed with the nuclear extract component. Results of the crosslinking studies suggested that proteins having relative molecular masses of approximately about 55 kDa and 150 kDa cross-linked to the probe fragment.

Figure 11:
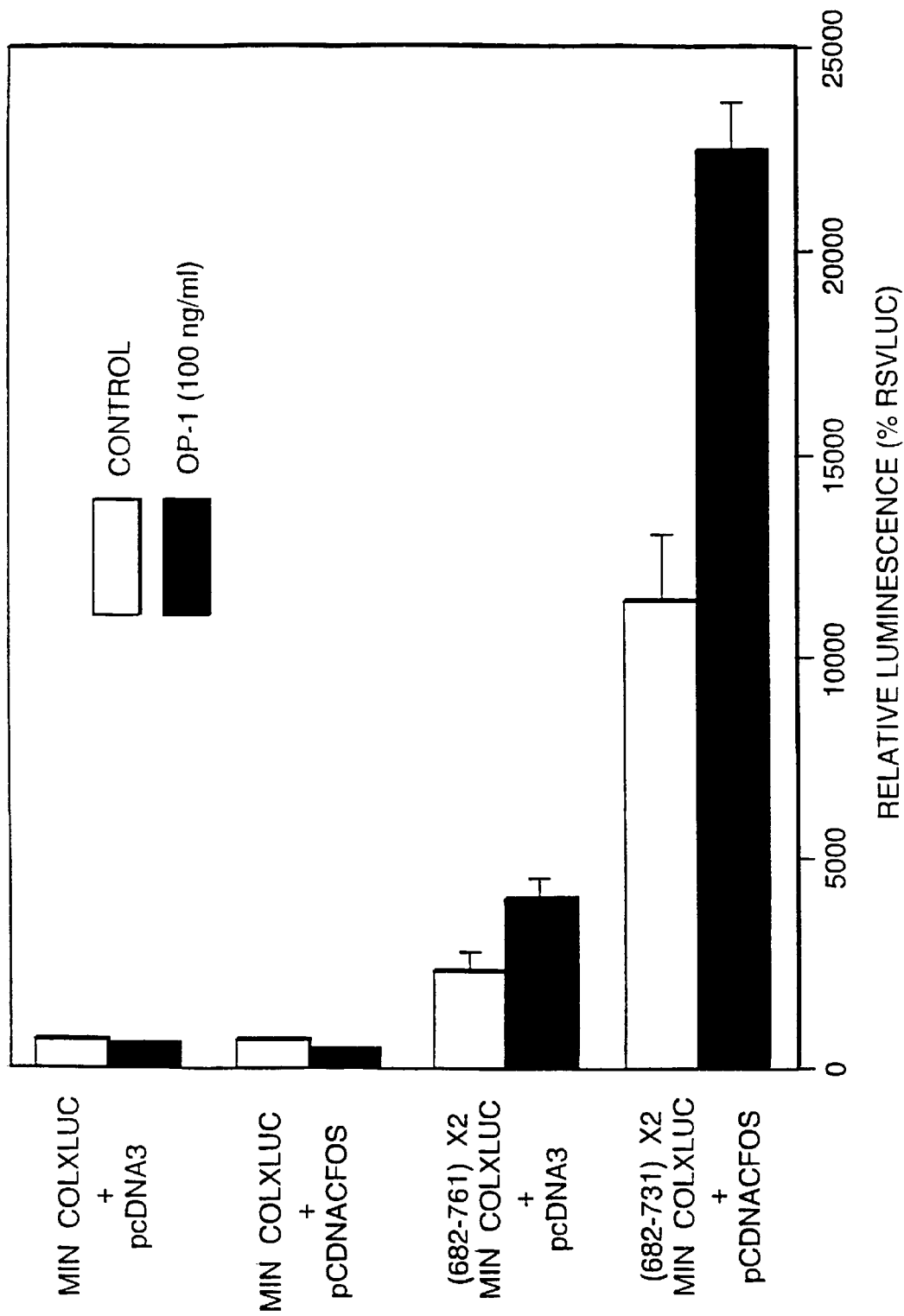
FIG. 11 is a bar graph depicting the stimulatory effect of c-fos coexpression on OP-1 induced luminescence produced by C5.18 cells transfected with reporter vectors containing the (nucleotides 682–761 of Seq. ID No. 1) mouse collagen type X promoter region.

To further examine the role of c-fos like proteins on the AP-1 like sequence in OP-1 driven up-regulation of the collagen type X promoter, an expression plasmid of human c-fos was co-transfected with the (682–761)x2-minCOLXLUC, which contains 2 copies of nucleotides 682–761 of SEQ. ID No. 1 upstream of the mouse collagen type X minimum promoter (nucleotides 919–1067 of SEQ. ID No. 1). Coexpression of c-fos increased the basal expression of the (682–761)x2-minCOLXLUC by two fold, and had no effect on the minCOLXLUC (FIG. 11). OP-1 further induced the expression of (682–761)x2-minCOLXLUC in the presence of human c-fos about 2 fold. These results suggest that the 682–761 nucleotides of SEQ. ID No. 1 interact with at least one other factor, required for OP-1 mediated regulation of the mouse collagen type X gene, which is distinct from the c-fos -like factor that interacts with the AP-1 site.

An A/T rich sequence (TTAAAAATAAA, SEQ. ID No. 9) of the collagen type X promoter resembles the consensus sequence of MEF-2 (SEQ. ID No. 6) (CTAAAAATAAC) (Yu et al. (1992) Genes Dev. 6:1783–1798). Gel shift assays with a 695–714 (SEQ. ID No. 1) probe showed that a major retarded band A and a weak band B were competed by excess cold homologous oligonucleotide as well as by the MEF-2 consensus oligonucleotide but not by oligonucleotides corresponding to other transcription factors NP, OCTA26, IgHOct or E-Box. A mutant variant of the oligonucleotide comprised of nucleotides 695–714 of SEQ. ID No. 1 (TTAAACATAAA SEQ. ID No. 7) analogous to a mutant MEF-2 consensus sequence (CTAAACATAAC SEQ. ID No. 8) and containing a mutation which abolishes its binding to MEF-2 protein, did not compete for the nuclear protein interaction with the collagen type X oligonucleotide (nucleotides 695–714 of SEQ. ID No. 1). However, a slower migrating band C was competed not only by homologous oligonucleotide but also by the mutant collagen type X (nucleotides 695–714 SEQ. ID No. 1), NP, OCTA26 or IgHOct oligonucleotides. These findings suggest specific binding of C5.18 nuclear proteins to the A/T rich sequence, analogous to the binding of MEF-2 to its consensus sequence. The collagen type X nucleotides 699–731 of SEQ. ID No. 1 thus interact with at least two distinct nuclear protein complexes present in C5.18 cells, via the 3'AP-1 like sequence and via the 5' A/T rich MEF-2 like sequence.

To further examine the mechanism for OP-1 upregulation of the collagen X promoter, the effects of OP-1 on the nuclear protein interaction with the AP-1 like sequence and the A/T rich, MEF-2 like sequence were examined. OP-1 treatment had no effect on the C5.18 nuclear protein interaction with the AP-1 like sequence, examined with the collagen type X probe (nucleotides 699–731 of SEQ. ID No. 1) with a mutation at the A/T rich sequence (see M2, FIG. 12). In contrast, gel shift assays using the (nucleotides 695–714 of SEQ. ID No. 1) probe showed that treatment of C5.18 cells with OP-1 (100 ng/ml) for 2 or 6 hours increased the intensity of a band (band A) up to 3–4 fold. OP-1 showed no effects on other bands, suggesting that OP-1 specifically increased the levels or the affinity of nuclear proteins which interact with the A/T rich sequence corresponding to band A within at least 2–12 hours and preferably within at least 2–6 hours after OP-1 treatment.

Still further characterization of the C5.18 nuclear proteins binding to the collagen type X A/T rich sequence revealed that, though they interact with the consensus MEF-2 site, they are distinct from MEF-2. OP-1 did not affect collagen type X promoter driven luciferase synthesis or collagen type X mRNA levels in C2C12 myoblasts which highly express MEF-2 proteins (see Table I). To characterize the C5.18 nuclear proteins which interact with the A/T rich sequence, and compare them with MEF-2, gel shift assays were performed using nuclear extracts from C5.18 cells and C2C12 myoblasts. Gel shift assays using the mouse collagen type X (nucleotides 695–714 of SEQ. ID No. 1) oligonucleotide probe showed that C2C12 nuclear proteins formed specific slow migrating complexes, which were also formed with C5.18 nuclear extracts with less intensity. These slow migrating bands were competed by cold homologous oligonucleotide and by the MEF-2 oligonucleotide (SEQ. ID No. 6). C2C12 nuclear extracts did not form a fast migrating complex formed by C5.18 nuclear extracts, suggesting cell type specificity for nuclear protein interaction with the A/T rich sequence. In contrast, gel shift assays using the (nucleotides 699–731 of SEQ. ID No. 1) oligonucleotide probe with a mutation in the A/T rich sequence (see M2, FIG. 12) showed that C2C12 nuclear proteins form an AP-1 complex similar to that formed by C5.18 nuclear extracts. C2C12 nuclear extracts also formed slow migrating complexes with the consensus MEF-2 probe (SEQ. ID No. 6), which were competed by cold homologous oligonucleotide but not by the mouse collagen type X (nucleotides 695–714 of SEQ. ID No. 1) oligonucleotide, nor by the mutant (nucleotides 695–714 of SEQ. ID No. 1) oligonucleotide, suggesting that the slow migrating bands correspond to the complexes formed by MEF-2 present in C2C12 myoblasts. The MEF-2 oligonucleotide probe also formed complexes with C5.18 nuclear extracts, however these were similar to the complexes formed with the collagen type X A/T rich sequence and were distinct from those formed by C2C12 nuclear extracts. The C5.18 nuclear protein interaction with the MEF-2 probe were competed by cold homologous oligonucleotide as well as to a lesser extent by the collagen type X (nucleotides 695–714 of SEQ. ID No. 1) oligonucleotide, but not by the mutant (nucleotides 695–714 of SEQ. ID No. 1) oligonucleotide. These results suggest that C5.18 cells express nuclear factors, distinct from MEF-2, which interact with the collagen type X A/T rich sequence and the MEF-2 sequence.

Thus, the OP-1 responsive transcription activating element in the mouse collagen type X gene promoter has been defined as containing at least two responsive sites and binding at least two substances present in nuclear extracts produced from OP-1 stimulated C5.18 cells. One such substance has the general immunological properties of a fos family protein and may be a novel member of the fos family. One other such substances shares similarities with an MEF-2 like protein. Thus, the appearance and specific biological effects and/or interactions of the fos-like protein and MEF-2 like protein with the collagen type X promoter offers unprecedented insight into the molecular basis of tissue-specific morphogenesis. This discovery is exploited, according to the present invention, for the identification of substances which can reproduce the specific biological effects and/or intracellular events induced by OP-1.

It is anticipated that tissue specificity of expression activator binding to the A/T rich sequence can be exerted in several ways. For example, the expression activators that bind to the A/T rich region and AP-1 like region, respectively, may interact directly with each other during the transcriptional activation process or may require the interaction of additional factors. It is further anticipated that a degree of synergism or inhibition of transcriptional activation will result upon interaction of the expression activators and that these interactions may be required for certain activities (e.g. tissue specificity) (Yu et al. (1992) *Genes Dev.* 6:1783–1798; the teachings of which are incorporated herein by reference). Yet further, it is anticipated that the sequences that flank the A/T rich and AP-1 like sequences of the transcription activating element are critical for sequence specific binding and/or for required or preferred aspects of transcriptional activation. For example, binding studies using oligonucleotides corresponding to alternative MEF-2 binding sequences showed differential binding activities depending upon the sequences flanking their identical core sequences (TTAAAAATAA; Yu et al. (1992) *Genes Dev.* 6:1783–1798)(SEQ ID NO:10). Still further, in the same study, MEF-2 peptide sequences lying well outside the shared MADS domain (e.g. 46 residues carboxy terminal to the MADS homology region) modulated the binding properties of the various MEF-2 isoforms.

In conclusion, a core 33 base pair OP-1 transcription activating element (nucleotides 699–731 of Seq. ID No. 1) contains an AP-1 like sequence and a MEF-2 like A/T rich sequence that are both required for OP-1 upregulation of collagen X promoter activity. Gel shift analysis shows that the C5.18 nuclear protein interaction with the AP-1 like sequence involves c-fos family which have previously been implicated in chondrogenesis and osteogenesis (Grigoriadis et al. (1995) *Trends Genet.* 11:436–441). C-fos and its family member, fra-2, are highly expressed in bone and cartilage during development (Dony and Gruss (1987) *Nature (London)* 328:711–714; Sandberg et al. (1988) *Development* 102:461–47) and transgenic mice overexpressing a c-fos transgene develop osteogenic and chondrogenic tumors (Grigoriadis et al. (1995) *Trends Genet.* 11:436–441). Indeed, BMP-2 and 3 have been shown to increase c-fos mRNA levels under low serum conditions in MC3T3-E1 osteoblastic cells (Ohta et al. (1992) *FEBS Lett.* 314:356–360). However, several observations presented here suggest that the induction or activation of c-fos itself is not the primary mechanism for OP-1 induction of collagen type X promoter activity. First, a mutation of the 33 base pair collagen type X promoter region at the MEF-2 like A/T rich sequence (M2, FIG. 12) abolished the activation by OP-1 but not the effect of bFGF, which induces c-fos mRNA in chondrocytes (Wroblewski and Edwall-Arvidsson (1995) *J. Bone Miner. Res.* 10:735–742). This result suggests that the AP-1 like sequence of M2 (FIG. 12), which is intact and still responds to bFGF, no longer responds to OP-1. Second, OP-1 failed to stimulate reporter activity driven by an AP-1 consensus sequence, while this reporter construct was induced by bFGF. Thirdly, OP-1 induced collagen X promoter activity when cotransfected with c-fos, which also increased the promoter activity by itself. Finally, OP-1 had no effect on C5.18 nuclear protein interaction with the AP-1 like sequence of the collagen X promoter, while it induced nuclear protein interaction with the A/T rich MEF-2 like sequence. Although activation of c-fos or AP-1 is not the primary target for OP-1 upregulation of collagen X promoter activity, the requirement for the AP-1 like sequence to achieve an OP-1 effect is of interest. AP-1 like sequences have been shown to play a role in activation of both the osteocalcin and the type I collagen promoters (Määttä et al. (1993) *Biochem. J.* 294:365–371; Schule et al. (1990) *Cell* 61:497–504). Moreover, AP-1 like sequences or Fos family proteins have been implicated in transcriptional regulation by TGF-β (Chang and Goldberg (1995) *J. Biol. Chem.* 270:4473–4477; Chung et al. (1996) *J. Biol. Chem.* 271:3272–3278; Datto et al. (1995) *J. Biol. Chem.* 270:28623–28628; Kerr et al. (1990) *Cell* 61:267–278). An AP-1 like sequence analogous to the AP-1 like sequence present in the collagen X promoter is also present in the rat osteocalcin promoter region responding to BMP-2 (Goto et al. (1994) *J. Bone Miner. Res.* 9 (*suppl.*1):s254 (abstract)). Further, a recent study suggests a role for AP-1 activity in the BMP-4 signaling pathway (Xu et al. (1996) *Proc. Natl. Acad. Sci. USA* 93:834–838).

In the present study, the mutation of the MEF-2 like sequence in the collagen X promoter region abolished OP-1 induction or promoter activity and nuclear protein binding to this region. Moreover, nuclear protein interaction with this sequence was specifically induced by OP-1 in C5.18 cells. Interestingly, OP-1 inducible MEF-2 like sequence Binding Activity ("OMBA") is not present in C2C12 myoblasts, which express MEF-2A, B, C and D, suggesting that the presence of MEF-2A-D proteins is not sufficient to confer OMBA in C2C12 cells. C2C12 cells respond to BMP-2 with expression of phenotypic markers for osteoblasts but not for chondrocytes (Katagiri et al. (1994) *J. Cell Biol.* 127:1755–1766). Consistent with this report, OP-1 had no effect on either the collagen X promoter or collagen X mRNA levels in C2C12 cells.

There are several transcription factors that interact with MEF-2 like sequences and form complexes migrating faster than those involving MEF-2 in gel shift assays: BBF-1 (Goswami et al. (1994) *Mol. Cell. Biol.* 14:5130–5138), ATF35 (Grayson et al. (1995) *Mol. Cell. Biol.* 15:1870–1878), an RSRF related A-rich binding factor (ARF) (Molkentin and Markham (1994) *Mol. Cell. Biol.* 14:5056–5065), HF-1b (Zhu et al. (1993) *Mol. Cell. Biol.* 13:4432–4444) and Gtx (Komuro et al. (1993) *EMBO J.* 12:1387–1401). Further, the homeodomain protein Mhox and the POU domain protein Oct-1 can interact with the MEF-2 site of the α-cardiac myosin heavy-chain gene (Cserjesi et al. (1994) *J. Biol. Chem.* 269:16740–16745). However, interaction of the OMBA with the collagen X MEF-2 like sequence is not competed by excess oligonucleotides corresponding to OCT or OCTA26 as well as NP oligonucleotides that were shown to compete for the binding of Gtx to the MEF-2 site (Komuro et al. (1993) *EMBO J.* 12:1387–1401). In addition, a point mutation of the collagen X MEF-2 like sequence, analogous to a mutant MEF-2 site which does not bind to MEF-2, abolished the OMBA. These results suggest that the OMBA recognizes a MEF-2 site analogous to the MEF-2 family and is distinct from homeodomain or POU domain proteins, including Gtx. Although MEF-2A, MEF-2C and MEF-2D bind to the same DNA sequence, subtle differences in binding affinity have been observed among these MEF-2 factors (Olson et al. (1995) Dev. Biol. 172:2–14). The DNA sequence surrounding the core consensus MEF-2 site also affects protein-DNA binding (Yu et al. (1992) Genes Dev. 6:1783–1798). OMBA binds to the collagen X MEF-2 like sequence as well as to a consensus MEF-2 site, while MEF-2, present in C2C12 cells, interacts preferentially with the MEF-2 site, suggesting that the OMBA possesses analogous but distinct affinity to MEF-2 like sequences.

MADS box proteins regulate programs of cell type specific gene expression in different organisms. In most cases, MADS box proteins exert these activities through cooperation with other regulatory factors. SRF interacts with a group of ETS-domain proteins, which bind a site adjacent to the serum response element in the c-fos promoter (Treisman, R. (1994) Curr. Opin. Genet. Dev. 4:86–101). MCM1 regulates cell type specific gene expression in the budding yeast Saccharomyces cerevisiae by acting in conjunction with two cell type specific coregulators, a homeodomain protein $\alpha$1, and a transcriptional repressor $\alpha$2 (Herskowitz, I. (1989) Nature (London) 342:749–757). MEF-2 has been shown to bind DNA cooperatively with myogenic basic helix-loop-helix (bHLH) proteins, resulting in synergistic activation of muscle-specific gene transcription. In fibroblasts, coexpression of MEF-2 and MyoD or myogenin dramatically increases the extent of myogenic conversion above that seen with either a myogenic bHLH factor or MEF-2 alone. A recent report showed that this cooperativity requires direct and specific interactions between DNA binding domains of MEF-2 and the myogenic bHLH factors (Molkentin et al. (1995) Cell 83:1125–1136). These reports are consistent with our finding that upregulation of collagen X promoter activity by OP-1 requires both OMBA, induced by OP-1 treatment, and AP-1.

Unlike the story unfolding in studies of myogenesis, where the MyoD family and MEF-2 family transcription factors act as master regulatory transcriptional switches (Olson and Klein (1994) Genes Dev. 8:1–8; Olson et al. (1995) Dev. Biol. 172:2–14), the mechanism controlling the expression of the chondrocyte specific genes is not well understood. Chondrocyte differentiation is marked by the sequential activation of many genes encoding cartilage matrix proteins such as proteoglycans, link protein, collagen type II, type IX, type XI and type X, and growth factors, hormones such as PTHrP (Lee et al. (1995) Endocrinology 136:453–463) FGFs (Crossley et al. (1996) Cell 84:127–136) and BMPs, and their receptors such as PTH/PTHrP receptor (Lee et al. (1995) Endocrinology 136:453–463) and FGF receptors (Szebenyi et al. (1995) Dev. Dyn. 204:446–456), suggesting the involvement of multiple transcription factors in this process (Cancedda et al. (1995) Int. Rev. Cytol. 159:265–358; Jacenko et al. (1991) Crit. Rev. Eukaryotic Gene Expr. 1:327–353). Indeed, functional analysis of type II or collagen X promoters in transgenic mice or in cell culture has identified multiple and distinct positive and negative regulatory sequences for chondrocyte specific expression of these genes (Long and Linsenmayer (1995) J. Biol. Chem. 270:31310–31314; Lu Valle et al. (1993) J. Cell. Biol. 121:1173–1179; Mukhopadhyay et al. (1995) J. Biol. Chem. 46:27711–27719; Zhou et al. (1995) J. Cell Sci. 108:3677–3684). An OP-1 response sequence has been identified which is active in C5.18 cells but not in NIH3T3, ROS17/2.8 or C2C12 cells, consistent with its effect on collagen X mRNA levels in these cells. However, significant differences in the basal collagen X promoter activity itself in these cells were not detected, suggesting the presence of additional positive and negative regulatory regions which also play a role in the cell type specific expression of collagen X mRNA in differentiated chondrocytes.

In summary, a specific responsive region for a morphogenic protein such as OP-1 has been identified in the collagen X promoter. Functional analysis of this region demonstrated the requirement for an AP-1 sequence and a MEF-2 sequence that interacts with nuclear factors induced by OP-1. Further characterization of these nuclear factors and their cooperation with the AP-1 like sequence should increase our molecular understanding of OP-1 induction of chondrocyte differentiation.

EXAMPLE 5

Purification of Sequence-Specific DNA Binding Proteins by Affinity Chromatography The above exemplified results provide clear evidence for the interaction of nuclear proteins with defined portions of the OP-1 transcription activation element of the mouse collagen type X promoter. Further to the identification of sites within the OP-1 transcription activating element by collagen type X promoter-luciferase deletion constructs, the identification of sequences that are protected by the binding of nuclear extracts to the transcription activating element, and of electrophoretic DNA band shift assays showing competition of specific retarded DNA-protein complexes, it is desirable to then isolate and characterize the specific DNA binding proteins required for OP-1 driven gene regulation. As discussed herein above, two such candidate binding proteins are members of the c-fos and MEF-2 families of transcription factors, respectively. It is anticipated that the DNA binding proteins disclosed herein will be purified, isolated and sequenced in accordance with routine practices as set forth below.

Methods for purifying sequence-specific DNA binding proteins by affinity chromatography are well known in the art (see Ausubel et al. (1995) Short Protocols in Molecular Biology, 3rd Edition, John Wiley & Sons, Inc., USA, chapter 12, pages 31–39, the methods of which are incorporated herein by reference). Briefly, synthetic oligonucleotides of specified sequence (e.g., the A/T rich or AP-1 like sequences of SEQ. No. 1) are annealed to make double stranded molecules, phosphorylated and ligated to produce multimerized oligonucleotides. The purified double stranded DNA is radiolabelled and incubated while stirring overnight at room temperature with 1 mM HCl hydrated CNBr-activated Sepharose 4B (Pharmacia Biotech) according to methods well known in the art (see Ausubel et al., 1995).

The oligonucleotide complexed resin is transferred to a scintered glass funnel and washed twice with 100 mls water and once with 100 mls 1M ethanol-aminohydrochoride, pH8.0. The level of radioactivity in the filtrate relative to the washed resin is used to estimate the efficiency of incorporation of DNA into the resin. 1M ethanolamine hydrochloride (pH8.0) is added to the resin until it is a smooth slurry and incubated at room temperature for 2–4 hours. The resin is washed with 100 ml 10 mM potassium phosphate (pH8.0), 100 ml 1M potassium phosphate (pH8.0). 100 ml 1M KCl, 100 ml water, and 100 ml of an appropriate column storage buffer.

For DNA affinity chromatography, 1 ml of the settled bed volume of DNA-coupled resin is equilibrated in a disposable chromatography column with two 10 ml washes of an appropriate column buffer/0.1M KCl. Crude protein extract is partially purified by conventional chromatography and the partially purified protein fraction is incubated with non-specific competitor DNA for 10 minutes on ice and centrifuged 10 minutes at 12,000×g 4° C. to pellet insoluble non-specific protein-DNA complexes. The supernatant is loaded onto the above prepared column and washed four times with 1 ml column buffer/0.1M KCl. The protein is eluted from the column by successive addition of 1 ml portions of column buffer containing 0.2M KCl, 0.3M KCl, 0.4M KCl, 0.5M KCl, 0.6 M KCl, 0.7 M KCl, 0.8 M KCl, and then 0.9M KCl, followed by three 1 ml additions of column buffer containing 1M KCl. One ml fractions are collected and assayed for sequence-specific DNA binding activity using an appropriate assay (e.g., a DNA binding assay such as the gel shift assay described in Example 4).

The isolation and characterization of the sequence-specific DNA binding proteins will require only routine experimentation using standard art known techniques. The above substantially purified eluate containing the DNA binding proteins can be enriched by filtration and concentration using Centricon micro concentrators (Amicon Corp.). It is contemplated that these proteins can be further purified according to charge by ion-exchange chromatography or according to size using gel filtration. Sequencing such proteins is achieved by standard N-terminal sequencing using an Applied Biosystems 477A Protein Sequencer. Results of previous crosslinking studies suggest that proteins that bind to the core 33 nucleotides (nucleotides 699–731 of SEQ. ID No. 1) may have, but are not limited to, molecular masses of approximately 55 kDa and 150 kDa. It is anticipated that the AP-1 like binding proteins will share sequence similarity to and antibody specificity with c-fos family proteins, such as the human c-fos p62 protein, a 64 kDa nuclear phosphoprotein. It is anticipated that the A/T rich protein will share sequence similarity to and antibody specificity with MEF-2 family proteins (e.g., MEF-2A/RSRFC/SL-2, MEF-2B/xMEF-2/RSRFR2, MEF-2c and MEF-2D/SL-1, which share homology in the MADS box domain and the adjacent region known as the MEF-2 domain, which have been isolated previously and implicated in skeletal and cardiac muscle cell differentiation (Olson et al. (1995) *Dev. Biol.* 172:2–14).

EXAMPLE 6

Cloning of Full Length DNA Binding Protein cDNAs and Genes

It is expected that cDNAs and genes corresponding to the DNA-binding proteins of the present invention will be prepared, isolated and sequenced in accordance with art-recognized protocols and routine experimentation. For example, in order to obtain a full length cDNA sequences encoding specific A/T rich region or AP-1 region binding proteins, a mouse cDNA library is created from the mRNA of OP-1 treated C5.18 cells and probed with, for example, the full length or partial c-fos p62 or MEF-2 protein cDNA, respectively, using routine methods. Alternatively, the mouse cDNA library may be probed with specific sequences corresponding to alternatively spliced isoforms of MEF-2, which have been found to determine their tissue specific expression (Yu et al. (1992) *Genes Dev.* 6:1783–1798). Several overlapping clones are obtained and their sequences are confirmed on both strands.

To obtain the corresponding DNA binding protein genes, a genomic mouse library such as any one of those available commercially, is probed with the full length DNA binding protein cDNAs. It is expected that the genes can be obtained and isolated, and their sequence determined by routine art known methods. Furthermore, genomic clones containing upstream promoter sequences are useful for promoter analyses.

For example, the DNA binding protein nucleotide sequences can be used as probes or the sequences can be modified to account for preferred codon bias (e.g., human codon bias) and used to probe cDNA or genomic libraries prepared from other species, e.g., humans, Drosophila, Xenopus, zebra fish, or rats. These homologues can be used in the same manner as is described below for mouse A/T rich region and AP-1 like region binding protein DNA sequences, i.e., as markers for morphogen responsiveness and to identify morphogen analogues.

Probes based on the nucleic acid sequences of the DNA binding proteins are synthesized on commercially available DNA synthesizers, e.g. Applied Biosystems model 381A, using standard techniques (e.g. in: Gait, *Oligonucleotide Synthesis: A Practical Approach,* IRL Press, Washington D.C., 1984). It is preferable that the probes are at least 8–50 bases long, more preferably 18–30 bases long. Probes are labeled in a variety of ways standard in the art, e.g. using radioactive, enzymatic or calorimetric labels as described, for example, by Berent et al. (Can/June 1985) *Biotechniques:* 208–220; and Jablonski et al, (1986) *Nucleic Acids Research* 14: 6115–6128.

Preferably, low stringency conditions are employed when screening a library for sequence-specific DNA binding protein homologs. Preferred specific probes are those corresponding to bases conserved between the known and other yet-to-be identified similar sequences.

For example, for a probe of about 20–40 bases a typical prehybridization, hybridization, and wash protocol is as follows: (1) prehybridization: incubate nitrocellulose filters containing the denatured target DNA for 3 hours at 55° C. in 5X Denhardt's solution, 6X SSC (20X SSC consists of 175 g NaCl, 88.2 g sodium citrate in 800 ml $H_2O$ adjusted to pH. 7.0 with 10N NaOH), 0.1% SDS, and 100 mg/ml denatured salmon sperm DNA, (2) hybridization: incubate filters in prehybridization solution plus probe at 42° C. for 24 hours, (3) wash; three 15 minutes washes in 6X SSC and 0.1% SDS at room temperature, followed by a final 1 minutes wash in 6x SSC and 0.1% SDS at 55° C. Other equivalent procedures, e.g. employing organic solvents such as formamide, are well known in the art.

Alternatively, sequence-specific DNA binding protein specific DNA can be amplified using a PCR methodology such as the one described below, to amplify approximately 500 base pair fragments. As for the hybridization screening probes described above, the primer sequences preferably are derived from sequences from conserved or other preferred domains.

Oligonucleotides are prepared with degeneracies introduced to include multiple probable sequences encoding the specific amino acid sequence, while maintaining the preferred species codon bias. In addition, where possible, observed conserved nucleotide sequences are exploited. These primers then are used in a PCR reaction using mRNA or genomic DNA of species of interest and standard procedures well known in the art, see for example, Saiki et al. (1985) *Science* 230:1350–1354. Briefly, degenerate oligonucleotides are synthesized on a standard automated DNA synthesizer, (e.g., Applied Biosystems Model 381A) following manufacturer's instructions, and then purified using standard procedures.

PCR reactions are performed with a commercially available thermal cycler and reagent kit (e.g., GeneAmp, Perkin & Elmer Corp., Norwalk) and following the manufacturer's instructions in a standard PCR protocol: in a 100 µl final volume with 1 µg genomic DNA, 1 mM final concentration of each primer, 0.2 mM dNTPs, 50 mM KCl, 10 mM Tris-HCl pH 9.0, 0.1% Triton X-100, 1.5 mM $MgCl_2$, 2.5 units of Taq polymerase. The reaction mixture is heated to 60° C. before addition of the nucleotides and polymerase and amplification is performed for 40 cycles:

| program: | 94° C. 1 min |
|---|---|
| | 55° C. 1 min. 30 sec. |
| | 72° C. 1 min. 20 sec. + |
| | 1 sec followed by a single extension of |
| | 72° C. 5 min. |
| | 4° C. hold |

Amplified products then are separated by standard polyacrylamide gel electrophoresis, and fragments of the appropriate size (e.g., 300–500 bases) excised and purified using standard procedures. These fragments then are subcloned into a standard, commercially available cloning vector (e.g., available from Invitrogen Inc., San Diego) compatible with the PCR-generated DNA fragment ends. DNA from individual clones then is prepared by standard alkaline lysis and the isolated DNAs sequenced using standard procedures and commercially available reagents (e.g., dideoxy sequencing, U.S. BioChem Sequencing Kit, Cleveland, Ohio.)

PCR amplified DNAs can then be used to create a probe (by random priming) for the screening of cDNA or genomic libraries of a species of interest under higher stringency conditions (e.g., washed at 0.1X SSC, 0.1% SDS, at 50° C.) to identify the complete coding sequences or genes using standard library screening procedures (see, for example, Maniatis, *Molecular Cloning: A Laboratory Manual* (2nd Ed'n, (1989) Cold Spring Harbor, N.Y.). Using standard probing procedures and appropriate hybridization conditions, homologues and other variants can be identified, including species variants.

It is anticipated that cDNAs corresponding to specific MEF-2 like A/T rich region binding proteins will confer OP-1 responsiveness to cells into which they have been transfected (Yu et al. (1992) *Genes Dev.* 6:1783–1798).

EXAMPLE 7

Preparation of Antibodies to Sequence Specific DNA Binding Proteins

Recombinantly produced DNA binding proteins capable of specific binding to the A/T rich and AP-1 like sequences can be used to obtain antibodies that are useful in immunoassays, as described below, and in the immunopurification of core DNA sequence binding proteins and variants thereof. Antibodies capable of specifically binding the DNA binding molecules in vivo can be used in immunohistochemical applications whereby the DNA binding molecules can be localized in tissue sections and sections of intact embryos. Such antibodies are useful for detecting the presence of A/T rich region and AP-1 region DNA binding proteins, which are indicators of morphogen responsiveness. Coupling DNA binding protein specific antibodies, or portions thereof, to immunohistochemical agents requires only routine skill; use of such coupled antibodies is in accordance with any number of well-known techniques for immunohistochemical localization.

For polyclonal antibodies, each rabbit is given a primary immunization (e.g., 500 mg) of purified or recombinantly-produced A/T rich or AP-1 like region binding protein, or protein fragments thereof in 0.1% SDS mixed with 500 ml Complete Freund's Adjuvant. The antigen is injected intradermally at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until the desired antibody is detected in the serum using a standard Western blot. Then, the rabbit is boosted monthly with 100 mg/ml of antigen and bled (15 ml per bleed) at days seven and ten after boosting.

Antiserum to sequence-specific DNA binding proteins is obtained using purified or recombinantly produced A/T rich or AP-1 like region binding protein as antigen and the polyclonal antibody production protocol described above. Antiserum reacts specifically with both the *E. coli*-produced and CHO-produced sequence-specific DNA binding proteins as determined by Western blot.

Similarly, monoclonal antibody specific for a given DNA binding molecule of interest can be prepared as described below. For example, a mouse is given two injections of substantially purified or recombinant DNA-binding protein or a protein fragment thereof. The first injection contains 100 mg of said protein in complete Freund's adjuvant and is given subcutaneously. The second injection contains 50 mg of said protein in incomplete adjuvant and is given intraperitoneally. The mouse then receives a total of 230 mg of said protein in four intraperitoneal injections at various times over an eight month period. One week prior to fusion, the mouse is boosted intraperitoneally with said DNA binding protein (e.g., 100 mg) and can be additionally boosted with a DNA binding protein-specific peptide conjugated to bovine serum albumin with a suitable crosslinking agent. This boost can be repeated five days (IP), four days (IP), three days (IP) and one day (IV) prior to fusion. The mouse spleen cells then are fused to commercially available myeloma cells at a ratio of 1:1 using PEG 1500 (Boehringer Mannheim, Germany), and the fused cells plated and screened, for example, A/T rich region or AP-1 like region specific DNA binding protein-specific antibodies using the desired DNA-binding protein as antigen. The cell fusion and monoclonal screening steps readily are performed according to standard procedures well described in standard texts widely available in the art. (See, for example, *Guide to Protein Purification* Murray P. Deutscher, ed., Academic Press, San Diego, 1990.)

EXAMPLE 8

Induction of Vascular Endothelial Growth Factor Expression by OP-1 in vitro and in vivo Angiogenesis is one of the earliest events in the transition from chondrogenesis to osteogenesis. Vascular endothelial growth factor (VEGF), the only secreted mitogen specific for vascular endothelial cells, has been implicated in physiological and pathological angiogenesis. Reports have indicated that VEGF expression in osteoblasts is increased by prostaglandin $E_1$ and $E_2$ and suppressed by glucocorticoids (Harada et al., (1994) *J. Clin. Invest.* 93: 2490–2496). Preliminary histochemical analysis of normal rat bone sections suggested that expression of VEGF could be localized in the hypertrophic zone of cartilage. This observation further suggested that VEGF may play a role in endochondral ossification. Thus, expression of VEGF is an indicator of endochondral bone formation induced by OP-1 and the OP-1 analogs disclosed herein, and can be measured in vivo by means of the following assay.

OP-1 -charged bone specific matrix pellets (Creative BioMolecules, Inc., Hopkinton, Mass.) were implanted in 4 week old male rats according to the earlier-referenced methods described in U.S. Pat. No. 4,968,590 and Sampath et al. (1983) Proc. Natl. Acad. Sci. USA 80:6591–6595. Following a suitable incubation period during which endochondral bone morphogenesis commenced, RNA extracted from nodules induced by OP-1 or a candidate compound. In the case of OP-1, VEGF mRNA was highly expressed at day 11 after implantation of OP-1, subsequent to the induction of type X collagen mRNA (at day 9). In OP-1 treated animals, VEGF mRNA was associated with hypertrophic chondrocytes, consistent with its expression at the growth plate region of long bones.

OP-1 also induced VEGF mRNA in vitro in C5.18 cells. VEGF mRNA peaked at 48 h after OP-1 treatment, following the induction of cartilage markers. In contrast, OP-1 had no effect on VEGF mRNA in RCT-3 osteoblastic cells. RCT-3 is a clonal cell line derived from retrovirus-immortalized embryonic rat calvaria cells which constitutively exhibits osteoblastic characteristics, as described by Heath et al. (1989) Endocrinology 124:3060:3068 and incorporated herein by reference. This observation suggests that the above-described effect on VEGF production was cell type specific. That is, TGFβ1-induced VEGF mRNA in both cell lines, but with a different time course (at 12 h). These observations demonstrate that VEGF mRNA is expressed during the morphogenetic transition from cartilage to bone in vivo and that OP-1 induced VEGF mRNA in chondro-osteo progenitor cells in vitro in a cell type specific manner. Analogs are expected to have similar induction effects.

EXAMPLE 9

Induction of Osteoblast Differentiation Markers

If desired, other cellular and molecular markers for tissue-specific, OP-1 induced morphogenesis may be monitored to confirm whether a test substance that reproduces the above-described intracellular events involving the type X collagen gene promoter indeed should be viewed as an OP-1 analog. Thus, PCT US92/07432 disclosed that OP-1 preferentially induces differentiation of uncommitted mammalian progenitor cells, including embryonic mesenchymal cells and primary osteoblasts. Potential analogs of OP-1 accordingly can be screened for a similar ability to induce differentiation of primary osteoblasts, by measuring the ability of these analogs to induce specific molecular markers such as alkaline phosphatase activity, PTH-mediated cAMP production and osteocalcin expression, all of which are induced when primary osteoblasts are exposed to morphogens such as human or mouse OP-1, the Drosophila homologue thereof, 60A, or human BMP2 or the Drosophila homologue thereof, DPP, or other members of the morphogen family.

Osteoblast-enriched primary cultures from a well-characterized model mammal, such as rat, preferably are used for the present corroborative studies. Although such cultures are heterogeneous in that the individual cells thereof are at different stages of differentiation, these cultures are believed to accurately reflect the metabolism and function of osteoblasts in vivo. Unless otherwise indicated, all chemicals referenced below are standard reagents, readily available from a number of commercial sources, including Sigma Chemical, Co., St. Louis; Calbiochem, Corp., San Diego and Aldrich Chemical Co., Milwaukee.

Rat osteoblast-enriched primary cultures are prepared by sequential collagenase digestion of newborn suture-free rat calvaria (e.g., from 1–2 day-old animals, Long-Evans strain, Charles River Laboratories, Wilmington, Mass.), following standard procedures, such as are described, for example, in Wong et al. (1975) Proc. Natl. Acad. Sci. 72:3167–3171. Rat osteoblast single cell suspensions then are plated onto a multi-well plate (e.g., a 24 well plate) at a concentration of 50,000 osteoblasts per well in αMEM (modified Eagle's medium, Gibco, Inc., Long Island) containing 10% FBS (fetal bovine serum), L-glutamine and a standard antibiotic, such as penicillin/streptomycin. The cells are incubated for 24 hours at 37° C. If appropriate under the circumstances, the growth medium is replaced with alpha MEM containing 1% FBS and the cells incubated for an additional 24 hours.

(a) Induction of Alkaline Phosphatase Activity in Osteoblasts

The cultured cells are incubated with OP-1, a suspected OP-1 analog or a negative control, using a range of concentrations. For example, 0.1, 1.0, 10.0, 40.0 or 80.0 ng OP-1/ml medium typically are used. 72 hours after the incubation period, the cell layer is extracted with 0.5 ml of 1% Triton X-100. The resultant cell extract then is centrifuged, and 100 µl of the extract is added to 90 µl of paranitrosophenylphospate (pNPP)/glycerine mixture and incubated for 30 minutes in a 37° C. water bath and the reaction stopped with 100 µl NaOH. The samples then are analyzed with a conventional spectrophotometric plate reader (e.g., the Dynatech MR700 plate reader). Absorbance is measured at 400 nm, using p-nitrophenol as a standard to determine the presence and amount of alkaline phosphate activity. Protein concentrations are determined by the BioRad method. Alkaline phosphatase activity is calculated in units/mg protein, where 1 unit=1 nmol p-nitrophenol liberated/30 minutes at 37° C. OP-1 induces a five-fold increase in the cellular specific activity of alkaline phosphate by this method. Analogs are expected to have similar induction effects.

(b) Induction of PTH-Mediated cAMP Production in Osteoblasts.

Primary cultures of mammalian, e.g., rat, osteoblasts are prepared and cultured in a multiwell plate as described above. The cultured cells then are divided into three groups: (1) wells which receive, for example, 1.0, 10.0 and 40.0 ng OP-1/ml medium); (2) wells which receive the candidate analog at various concentration ranges; and (3) a control group which receives equivalent volumes of the medium used for diluting the OP-1 or analog thereof. The plate is then incubated for another 72 hours. Thereafter, the cells are treated with medium containing 0.5% bovine serum albumin (BSA) and 1 mM 3-isobutyl-1-methylxanthine for 20 minutes followed by the addition, into half of the wells, of human recombinant parathyroid hormone (hPTH, Sigma, St. Louis) at a concentration of 200 ng/ml for 10 minutes. The cell layer then is extracted from each well with 0.5 ml of 1% Triton X-100. Cyclic AMP levels then are determined using a widely available radioimmunoassay kit (e.g., Amersham, Arlington Heights, Ill.). OP-1 doubles cAMP production in the presence of PTH. Analogs are expected to have similar induction effects.

(c) Induction of Osteocalcin Production in Osteoblasts

Osteocalcin is a bone-specific protein produced by osteoblasts and secreted into the circulation. Osteocalcin plays an integral role in regulating the rate of bone mineralization in mammals. Accordingly, serum levels of osteocalcin can be monitored as an indicator of osteoblast activity and bone formation in vivo. Similarly, induction of osteocalcin synthesis in osteoblast-enriched cultures can be used to corroborate whether a suspected OP-1 analog indeed can reproduce systemic effects of OP-1 treatment.

Rat osteoblasts are prepared and cultured in a multi-well plate as above. For osteocalcin analysis, the medium contains 10% FBS, and on day 2, cells are fed with fresh medium supplemented with fresh 10 mM β-glycerophosphate (Sigma, Inc.). Beginning on day 5 and twice weekly thereafter, cells are fed with a complete mineralization medium containing all of the above components plus fresh L(+)-ascorbate, at a final concentration of 50 mg/ml medium. OP-1 or OP-1 analog then is added to the wells directly, e.g., in 50% acetonitrile (or 50% ethanol) containing 0.1% trifluoroacetic acid (TFA), at no more than 5 mg OP-1/ml medium. Control wells receive solvent vehicle only. The cells then are re-fed and the conditioned medium sample diluted 1:1 in standard radioimmunoassay buffer containing standard protease inhibitors and stored at −20° C. until assayed for osteocalcin. Osteocalcin synthesis is measured by standard radioimmunoassay using a commercially available osteocalcin-specific antibody and can be confirmed by Northern blot analysis to calculate the amount of osteocalcin mRNA produced in the presence and absence of OP-1 or an OP-1 analog. OP-1 induces a dose-dependent increase in osteocalcin production (5-fold increase using 25 ng of OP-1 protein/ml), and a 20-fold increase in osteocalcin mRNA. Analogs are expected to have similar induction effects.

Mineralization is determined on long term cultures (13 day) using a modified Von Kossa staining technique on fixed cell layers: Cells are fixed in fresh 4% paraformaldehyde at 23° C. for 10 min, following rinsing cold 0.9% NaCl. Fixed cells then are stained for endogenous alkaline phosphatase at pH 9.5 for 10 min, using a commercially available kit (Sigma, Inc., St. Louis, Mo.). Purple stained cells then are dehydrated with methanol and air dried. After 30 min incubation in 3% $AgNO_3$ in the dark, $H_2O$-rinsed samples are exposed for 30 sec to 254 nm UV light to develop the black silver-stained phosphate nodules. Individual mineralized foci (at least 20 mm in size) are counted under a dissecting microscope and expressed as nodules/culture. OP-1 induces a 20-fold increase in initial mineralization rate. Analogs are expected to have similar induction effects.

EXAMPLE 10

Induction of Neuronal Markers by Morphogen Analogs: CAM Expression

It is further expected that the OP-1 2nd morphogen analogs contemplated herein will induce CAM expression, particularly N-CAM expression, as part of their induction of morphogenesis. CAMs are morphoregulatory molecules identified in all tissues, especially nerve tissues, as an essential step in tissue development. N-CAMs, which comprise at least 3 isoforms (N-CAM-180, N-CAM-140 and N-CAM-120, where "180", "140" and "120" indicate the apparent molecular weights of the isoforms as measured by polyacrylamide gel electrophoresis) are expressed at least transiently in developing tissues, and permanently in nerve tissue. Both the N-CAM-180 and N-CAM-140 isoforms are expressed in both developing and adult tissue. The N-CAM-120 isoform is found only in adult tissue. Another neural CAM is L1.

N-CAMs are particularly useful as indicators of neuronal-specific tissue morphogens or analogs thereof. They are implicated in appropriate neural development, including appropriate neurulation, neuronal migration, fasciculation, and synaptogenesis. Inhibition of N-CAM production, as by complexing the molecule with an N-CAM-specific antibody, inhibits retina organization, including retinal axon migration, and axon regeneration in the peripheral nervous system, as well as axon synapses with target muscle cells. In addition, significant evidence indicates that physical or chemical trauma to neurons, oncogenic transformation and some genetic neurological disorders are accompanied by changes in CAM expression, which alter the adhesive or migratory behavior of these cells. Furthermore, increased N-CAM levels are reported in Huntington's disease striatum (e.g., striatal basal ganglia), and decreased adhesion is noted in Alzheimer's disease.

The OP-1 and morphogen analogs contemplated herein are expected to stimulate CAM production, particularly L1 and N-CAM production, including all three isoforms of the N-CAM molecule. For example, N-CAM expression can be stimulated significantly in morphogen-treated NG108-15 cells as earlier described in U.S. Ser. No. 08/260,675, the disclosure of which is incorporated herein by reference; and in Perides et al. (1994) *J. Biol. Chem.* 269:765–770 and (1993) *J. Biol. Chem.* 268:25197–25205, the disclosures of which are also incorporated herein by reference. NG108-15 is a transformed hybrid cell line (neuroblastoma x glioma, American Type Culture Collection, Rockville, Md.) exhibiting a morphology characteristic of transformed embryonic neurons. Untreated NG108-15 cells exhibit a fibroblastic, or minimally differentiated morphology and express only the 180 and 140 isoforms of N-CAM normally associated with a developing cell. Following morphogen, e.g., OP-1, treatment, these cells exhibit a morphology characteristic of adult neurons and express enhanced levels of all three N-CAM isoforms. Using a protocol similar to that described below, treatment of NG108-15 cells with OP-1 or morphogen analogs will to the same extent as authentic OP-1 induce L1 expression.

NG108-15 cells are cultured for 4 days in the presence of increasing concentrations of OP-1 or OP-1 analogs, and standard Western blots are then performed on whole cells extracts. N-CAM isoforms are detected with an antibody which crossreacts with all three isoforms, mAb H28.123, obtained from Sigma Chemical Co., St. Louis, the different isoforms being distinguishable by their different mobilities on an electrophoresis gel. Control NG108-15 cells (untreated) will express both the 140 kDa and the 180 kDa isoforms, but not the 120 kDa, as determined by western blot analyses using up to 100 mg of protein. Treatment of NG108-15 cells with OP-1 will result in a dose-dependent increase in the expression of the 180 kDa and 140 kDa isoforms, as well as the induction of the 120 kDa isoform. Additionally, an increase in N-CAM expression will correspond in a dose-dependent manner with the morphogen induction of multicellular aggregates. Standard immunolocalization studies performed with the mAb H28.123 on treated cells will show N-CAM cluster formation is associated with the periphery and processes of treated cells. Moreover, treatment will not inhibit cell division as determined by cell counting or $^3$H-thymidine uptake. Furthermore, these cell aggregation effects of OP-1 or OP-1 analogs on NG108-15 cells can be inhibited with anti-N-CAM antibodies or antisense N-CAM oligonucleotides. Antisense oligonucleotides can be made synthetically on a nucleotide synthesizer, using standard means known in the art. Preferably, phosphorothioate oligonucleotides ("S-oligos") are prepared, to enhance transport of the nucleotides across cell membranes. Concentrations of both N-CAM antibodies and N-CAM antisense oliognucleotides sufficient to inhibit N-CAM induction also inhibited formation of multilayered cell aggregates. Specifically, incubation of NG108-115 cells with 0.3–3 mM N-CAM antisense S-oligos, 5–500 mM unmodified N-CAM antisense oligos, or 10 mg/ml mAb H28.123 will significantly inhibit cell aggregation.

The efficacy of morphogen analog treatment on N-CAM expression in vivo may be evaluated by tissue biopsy using routine methods and immunohistochemistry by detecting N-CAM molecules with an N-CAM-specific antibody, such as mAb H28.123. Alternatively, the level of N-CAM proteins or protein fragments present in cerebrospinal fluid or serum also may be detected to evaluate the effect of treatment. N-CAM molecules are known to slough off cell surfaces and have been detected in both serum and cerebrospinal fluid. In addition, altered levels of the soluble form of N-CAM are associated with normal pressure hydrocephalus and type II schizophrenia. N-CAM fluid levels may be detected using an N-CAM specific antibody, such as mAb H28.123 using routine immunoassay procedures.

EXAMPLE 11

General Formulation and Administration Considerations

Morphogen analogs, including OP-1 analogs, can be formulated for administration to a mammal, preferably a human in need thereof as part of a pharmaceutical composition. The composition can be administered by any suitable means, e.g., parenterally, orally or locally. Where the morphogen analog is to be administered locally, as by injection, to a desired tissue site, or systemically, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the composition preferably comprises an aqueous solution. The solution preferably is physiologically acceptable, such that administration thereof to a mammal does not adversely affect the mammal's normal electrolyte and fluid volume balance. The aqueous solution thus can comprise, e.g., normal physiologic saline (0.9% NaCl, 0.15M), pH7–7.4.

Useful solutions for oral or parenteral systemic administration can be prepared by any of the methods well known in the pharmaceutical arts, described, for example, in *Remington's Pharmaceutical Sciences*, (Gennaro, A., ed., Mack Pub., 1990). Formulations can include, for example, polyalkylene glycols such as polyethylene glycol, oils of vegetable origin, hydrogenated naphthalenes, and the like. Formulations for direct administration, in particular, can include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the morphogen analog in vivo.

Other potentially useful parenteral delivery systems for the present analogs can include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate or deoxycholate, or oily solutions for administration in the form of nasal drops or as a gel to be applied intranasally.

Alternatively, the morphogen analogs, including OP-1 analogs, identified as described herein may be administered orally. For example, liquid formulations of morphogen analogs can be prepared according to standard practices such as those described in *Remington's Pharmaceutical Sciences* (Gennaro, A., ed.; Mack Pub., 1990), the disclosure of which is incorporated herein by reference. Such liquid formulations can then be added to a beverage or another food supplement for administration. Oral administration can also be achieved using aerosols of these liquid formulations. Alternatively, solid formulations prepared using art-recognized emulsifiers can be fabricated into tablets, capsules or lozenges suitable for oral administration.

Optionally, the analogs can be formulated in compositions comprising means for enhancing uptake of the analog by a desired tissue. For example, tetracycline and diphosphonates (bisphosphonates) are known to bind to bone mineral, particularly at zones of bone remodeling, when they are provided systemically in a mammal. Accordingly, such components can be used to enhance delivery of the present analogs by bone tissue. Alternatively, an antibody or portion thereof that binds specifically to an accessible substance specifically associated with the desired target tissue, such as a cell surface antigen, also can be used. If desired, such specific targeting molecules can be covalently bound to the present analog e.g., by chemical crosslinking, or by using standard genetic engineering techniques to create, for example, an acid labile bond such as an Asp-Pro linkage. Useful targeting molecules can be designed, for example, according to the teachings of U.S. Pat. No. 5,091,513.

Still further, the present analogs can be administered to the mammal in need thereof either alone or in combination with another substance known to have a beneficial effect on tissue morphogenesis. Examples of such substances (herein, cofactors) include substances that promote tissue repair and regeneration and/or inhibiting inflammation. Examples of useful cofactors for stimulating bone tissue growth in osteoporotic individuals, for example, include but are not limited to, vitamin $D_3$, calcitonin, prostaglandins, parathyroid hormone, dexamethasone, estrogen and IGF-I or IGF-II. Useful cofactors for nerve tissue repair and regeneration can include nerve growth factors. Other useful cofactors include symptom-alleviating cofactors, including antiseptics, antibiotics, antiviral and antifungal agents and analgesics and anesthetics.

Analogs preferably are formulated into pharmaceutical compositions by admixture with pharmaceutically acceptable, nontoxic excipients and carriers. As noted above, such compositions can be prepared for systemic, e.g., parenteral, administration, particularly in the form of liquid solutions or suspensions; for oral administration, particularly in the form of tablets or capsules; or intranasally, particularly in the form of powders, nasal drops or aerosols. Where adhesion to a tissue surface is desired, the composition can comprise a fibrinogen-thrombin dispersant or other bioadhesive such as is disclosed, for example in PCT US91/09275, the disclosure of which is incorporated herein by reference. The composition then can be painted, sprayed or otherwise applied to the desired tissue surface.

The compositions can be formulated for parenteral or oral administration to humans or other mammals in therapeutically effective amounts, e.g., amounts which provide appropriate concentrations of the morphogen analog to target tissue for a time sufficient to induce the desired effect. Preferably, the present compositions alleviate or mitigate the mammal's need for a morphogen-associated biological response, such as maintenance of tissue-specific function or restoration of tissue-specific phenotype to senescent tissues (e.g., osteopenic bone tissue).

As will be appreciated by those skilled in the art, the concentration of the present morphogen analogs in compositions formulated for administration to mammals will vary depending upon a number of factors, including the dosage of the particular analog to be administered, the chemical characteristics (e.g., hydrophobicity) of the analog employed, the route of administration, and frequency or duration of administration. The preferred dosage of analog to be administered also is likely to depend on such variables as the type and extent of tissue loss or defect, the overall health status of the particular mammal, the relative biological efficacy or toxicity of the analog selected, the formulation of the compound, and the presence and types of excipients in the formulation.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for identifying a compound capable of activating an OP-1-responsive transcription activating element, the method comprising the steps of:
   (a) obtaining a recombinant cell transformed with DNA comprising an OP-1-responsive transcription activating element in operable association with a reporter gene;
   (b) exposing said cell to a candidate compound; and
   (c) determining whether said reporter gene is expressed, said expression being indicative that said candidate compound is capable of inducing expression of an OP-1-responsive transcription activating element.

2. The method of claim 1 wherein said OP-1-responsive transcription activating element is capable of binding to a member of the MEF-2 family of proteins.

3. The method of claim 1 wherein said OP-1-responsive transcription activating element comprises nucleotides 699–731 of SEQ ID NO:1.

4. The method of claim 1 wherein said OP-1-responsive transcription activating element comprises nucleotides 682–761 of SEQ ID NO:1.

5. The method of claim 1 wherein said OP-1-responsive transcription activating element comprises an AP1 binding site comprising nucleotides selected from the group consisting of: nucleotides 715–724 of SEQ ID NO:1, and SEQ ID NO:2.

6. A method for identifying a compound capable of binding to DNA, the sequence of said DNA comprising nucleotides 699–731 of SEQ ID NO:1, the method comprising the steps of:
   (a) exposing said DNA to a candidate compound; and,
   (b) detecting the binding of said candidate compound to said DNA.

7. An isolated nucleic acid comprising a sequence selected from the group consisting of: nucleotides 699–731 of SEQ ID NO:1, nucleotides 682–731 of SEQ ID NO:1, and nucleotides 682–761 of SEQ ID NO:1.

8. The isolated DNA sequence of claim 7 wherein said DNA sequence comprises an MEF-2 binding site sequence adjacent an AP1 binding site sequence.

9. A cell transfected with a nucleic acid of claim 7 or 8.

* * * * *